United States Patent [19]

Toth et al.

[11] Patent Number: 5,258,406
[45] Date of Patent: Nov. 2, 1993

[54] SULFONIMIDAMIDES

[75] Inventors: John E. Toth; James E. Ray, both of Indianapolis, Ind.

[73] Assignee: Eli Lilly and Company, Indianapolis, Ind.

[21] Appl. No.: 993,506

[22] Filed: Dec. 16, 1992

Related U.S. Application Data

[63] Continuation of Ser. No. 812,259, Dec. 20, 1991, abandoned.

[51] Int. Cl.$^5$ .................. A61K 31/175; A61K 31/16; C07D 309/00; C07C 313/00
[52] U.S. Cl. .................................... 514/593; 514/607; 514/608; 549/356; 549/369; 549/362; 549/377; 560/142; 564/101
[58] Field of Search .................. 514/593, 607, 608; 549/356, 362, 369, 377; 560/142; 564/101

[56] References Cited

U.S. PATENT DOCUMENTS

| | | | |
|---|---|---|---|
| 3,097,242 | 7/1963 | Hoehn et al. | 260/553 |
| 3,102,115 | 8/1963 | Breuer et al. | 260/239 |
| 3,102,121 | 8/1963 | Breuer et al. | 260/330.5 |
| 3,736,122 | 5/1973 | Tung et al. | 71/103 |
| 3,849,110 | 11/1974 | Soper et al. | 71/103 |
| 4,666,506 | 5/1987 | Hillemann | 71/90 |
| 4,845,128 | 7/1989 | Harper et al. | 514/592 |
| 4,952,698 | 8/1990 | Biere et al. | 548/131 |
| 5,104,417 | 4/1992 | Crowell et al. | 44/280 |
| 5,110,830 | 5/1992 | Harper et al. | 514/592 |
| 5,116,874 | 5/1992 | Poore | 514/592 |
| 5,140,026 | 8/1992 | Hellberg et al. | 514/238.2 |
| 5,187,189 | 2/1993 | Hellberg et al. | 514/608 |

FOREIGN PATENT DOCUMENTS

| | | |
|---|---|---|
| 107214 | 9/1983 | European Pat. Off. |
| 166615 | 1/1986 | European Pat. Off. |
| 222475 | 5/1987 | European Pat. Off. |
| 254577 | 1/1988 | European Pat. Off. |
| 291269 | 11/1988 | European Pat. Off. |

OTHER PUBLICATIONS

C. Rees, et al., *Journal of the Chemical Society (London)*, (C):1474 (1969).
R. Grice and L. Owens, *Journal of the Chemical Society (London)*, 1947 (1963).
D. Harpp, et al., *Synthesis*, 181 (1979).
R. Young, et al., *Tetrahedron Letters*, 25:1753 (1984).
G. B. Grindey, et al., *Proceedings of the American Association of Cancer Research*, 27:277 (Abstrct 1099) (1986).
J. J. Howbert, et al., *JOurnal of Medicinal Chemistry*, 33:2393 (1990).
G. Jähnchen, et al., *Zeitschrift Chem.*, 39:305 (1969).
C. Goralski, et al., *Journal of Chemical and Engineering Data*, 21:237 (1976).
F. Kurzer, *Organic Synthesis Coll.*, vol. IV, 937 (1963).
C. Johnson, et al., *Journal of Organic Chemistry*, 44:2055 (1979).
J. Yuon, et al., *Synthesis*, 72 (1987).
J. Huon, et al., *Tetrahedron Letters*, 27:1493 (1986).

*Primary Examiner*—José G. Dees
*Assistant Examiner*—Ponfirio Nazario
*Attorney, Agent, or Firm*—Paul J. Gaylo; Leroy Whitaker; David E. Boone

[57] ABSTRACT

This invention provides certain sulfonimidamide compounds, formulations and method of use of these compounds in treating susceptible neoplasms.

15 Claims, No Drawings

SULFONIMIDAMIDES

This application is a continuation of application Ser. No. 07/812,259, filed on Dec. 20, 1991, now abandoned.

FIELD OF THE INVENTION

This invention relates to certain sulfonimidamides and their use as antineoplastic agents.

BACKGROUND OF THE INVENTION

Cancer is one of the leading causes of death in the United States. The American Cancer Society reports that about 494,000 people died from cancer in the United States in 1988. A common method of treatment for cancer is the use of chemotherapy. The use of chemotherapy has not been particularly successful in the treatment of solid tumors. Accordingly, there is a substantial need for new drugs which are effective in inhibiting the growth of such tumors.

It has now been found that a new group of sulfonimidamides have been effective in inhibiting the growth of solid tumors.

Certain diarylsulfonylureas have been reported as being active antitumor agents. U.S. Pat. No. 4,845,128 of Harper et al. (1989), Grindey et al., Proc. American Association of Cancer Research, vol. 27 page 277 (1986), and Howbert et al., Journal of Medicinal Chemistry, 33, 2393 (1990). These references are all directed to sulfonylureas and there is no suggestion or disclosure of the sulfonimidamides of the instant invention.

Certain sulfonimidamides have been reported. Johnson et al., Journal of Organic Chemistry, 44, 2055 (1979) discloses the preparation of certain of such compounds. One such compound, N-butyl-N'-(p-toluenesulfonimidoyl)urea (compound 16), is disclosed as being inactive in an antidiabetic screen. There is no disclosure of the instant compounds of their use in inhibiting the growth of neoplasms.

U.S. Pat. No. 4,666,506 of Hillemann (1987) discloses a large number of aryl and heteroaryl sulfonimidamides for use as herbicides and/or plant growth regulants. There is no suggestion or disclosure in this reference of the compounds of the instant invention.

SUMMARY OF THE INVENTION

In one embodiment the present invention comprises compounds of the formula 1

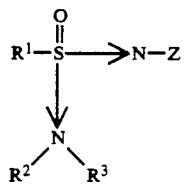

wherein $R^1$ is

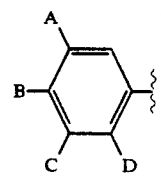

wherein A, B and C are independently: hydrogen, with the proviso that at least one of A, B or C is other than hydrogen; chlorine, bromine or iodine; methyl or ethyl; —C(O)$R^a$, wherein $R^a$ is hydrogen or $C_1$–$C_5$ alkyl; —(CH$_2$)$_n$O$R^b$ wherein n is 1–4 and $R^b$ is hydrogen or C(O)$R^c$ wherein $R^c$ is $C_1$–$C_4$ alkyl; or A and B or B and C together are —(CH$_2$)$_q$— wherein q is 3 or 4, —(CH$_2$)$_m$O(CH$_2$)$_b$— wherein m is 0 or 1 and b is 1, 2 or 3 with the proviso that b is 2 or 3 when m is 0, or —O—(CH$_2$)$_n$—O— wherein n is 1 or 2 and C or A respectively is hydrogen or CH$_3$; and D is hydrogen, chlorine, bromine, iodine, methyl, or ethyl; and $R^2$ is hydrogen, $C_1$–$C_8$ alkyl with the proviso that except for the isopropyl group there is no branching in the alpha-position, $C_3$–$C_8$ alkenyl, —(CH$_2$)$_n$OH wherein n is 1–5, —(CH$_2$)$_p$C$_6$H$_5$ wherein p is 1–3, or —C(O)$R^d$ wherein $R^d$ is hydrogen or $C_1$–$C_4$ alkyl;

$R^3$ is hydrogen or methyl; and

Z is

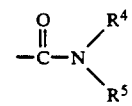

wherein $R^4$ is hydrogen, methyl, or —C(O)$R^a$ wherein $R^1$ is hydrogen or $C_1$–$C_5$ alkyl;

$R^5$ is

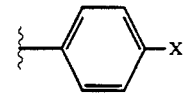

wherein X is chlorine, bromine, iodine or methyl;
or a tautomer
or a pharmaceutically acceptable salt thereof.

In another embodiment, the present invention comprises a pharmaceutical formulation containing a compound of formula 1 or a pharmaceutically acceptable salt thereof in combination with a pharmaceutically acceptable excipient.

In a further embodiment of the present invention comprises a method for treating susceptable neoplasms in mammals which comprises administering to a mammal in need of such treatment an effective amount of a compound of formula 1 or a pharmaceutically salt thereof.

DETAILED DESCRIPTION OF THE INVENTION

As used herein the following terms shall have the indicated meanings.

The term "$C_1$–$C_8$ alkyl" refers to straight and branched chain alkyl groups having from one to eight carbon atoms provided that except for the isopropyl group there is no branching at the alpha carbon, including without limitation methyl, ethyl, n-propyl, isopropyl, n-butyl, isobutyl, 3-methylpentyl, n-heptyl, 3-ethylpentyl, and the like. The alpha carbon is the first carbon in the alkyl chain, e.g., the methylene moiety in an ethyl group. The term "$C_1$–$C_3$ alkyl" refers to methyl, ethyl, n-propyl and isopropyl. The term "$C_1$–$C_5$ alkyl" refers to straight and branched chain alkyl groups having one to five carbon atoms.

The term "C₃-C₈ alkenyl" refers to straight and branched chain unsaturated alkyl groups having from three to eight carbon atoms provided there is a single bond between the alpha and beta carbons and further provided that except for 1-methylethene there is no branching at the alpha carbon. Such groups include 1-propenyl, 1-methyl-1-propenyl, 1-butenyl, 1-hexenyl, 2-methylpropenyl and the like.

Compounds of the instant invention in which A and B together of $R^1$ are —(CH2)q where q is 3 and C and D are each hydrogen have the following structure:

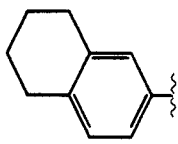

When B and C together are —(CH$_2$)$_m$O(CH$_2$)$_b$— in which m is 1, b is 2 and A and D are each hydrogen, the following structures are provided.

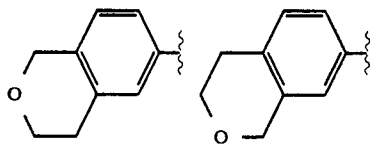

When A and B together are —O(CH$_2$)$_n$—O— and C and D are hydrogen, the following structure is provided when n is 2.

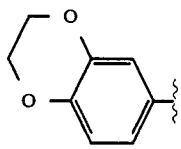

Preferred compounds of the instant invention are those of formula 1 in which $R^1$ is

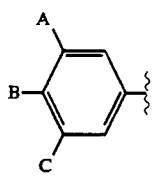

wherein A and C are independently hydrogen or methyl; B is chlorine, bromine, methyl, CH$_2$OH, C(O)H, CH$_2$OC(O)CH$_3$, or CH$_3$CH$_2$; or A and B together are —(CH$_2$)$_3$— and C is hydrogen or methyl; $R^2$ is C$_1$-C$_4$ alkyl, hydrogen, or CH$_3$C(O); $R^3$ is hydrogen; $R^4$ is hydrogen or methyl; and $R^5$ is parachlorophenyl, parabromophenyl or paramethylphenyl.

More preferred compounds of formula 1 include: N-[[(4-chlorophenyl)amino]carbonyl]-4-methylbenzenesulfonimidamide, N-[[(4-chlorophenyl)amino]carbonyl]-N'-4-dimethylbenzenesulfonimidamide, N-[[(4-chlorophenyl)amino]carbonyl]-N'-ethyl-4-methylbenzenesulfonimidamide, N-[[(4-chlorophenyl)amino]carbonyl]-N'-(1-methylethyl)-4-methylbenzenesulfonimidamide, N-[[(4-chlorophenyl)amino]carbonyl]-N'-butyl-4-methylbenzenesulfonimidamide, N-[[(4-chlorophenyl)amino]carbonyl]-N'-acetyl-N'-methyl-4-methylbenzenesulfonimidamide, N-methyl-N-[[(4-chlorophenyl)amino]carbonyl]-4-methylbenzenesulfonimidamide, N-[[(4-bromophenyl)amino]carbonyl]-4-methylbenzenesulfonimidamide, N-[[(4-chlorophenyl)amino]carbonyl]-4-ethylbenzenesulfonimidamide, N-[[(4-chlorophenyl)amino]carbonyl]-3,4-dimethylbenzenesulfonimidamide, N-[[(4-chlorophenyl)amino]carbonyl]-N'-butyl-4-methylbenzenesulfonimidamide, N-[[(4-chlorophenyl)amino]carbonyl]-3,4,5-trimethylbenzenesulfonimidamide, N-[[(4-chlorophenyl)amino]carbonyl]-4-(acetoxymethyl)benzenesulfonimidamide, N-[[(4-chlorophenyl)]amino]carbonyl]-4-(hydroxymethyl)benzenesulfonimidamide, N-[[(4-chlorophenyl)amino]carbonyl]-4-formylbenzenesulfonimidamide, N-[[(4-chlorophenyl)amino]carbonyl]-5-indanylsulfonimidamide, and N-[[(4-chlorophenyl)amino]carbonyl]-N'-methyl-5-indanylsulfonimidamide.

The instant compounds are named herein as sulfonimidamides. This refers to compounds having a sulfur atom which is covalently bonded to a carbon, oxygen and two nitrogen atoms. This structure is represented in formula 1 as:

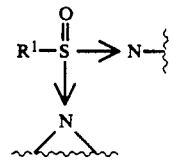

Formally the bond between the sulfur and one of the nitrogens is a double bond while the other is single. The possible tautomers are represented as A and B below:

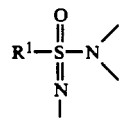

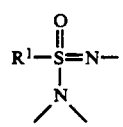

It has been reported by Johnson et al., *J. Org. Chem.*, 44, at page 2056, that the tautomeric forms A and B may be in rapid equilibrium when there is a hydrogen on either of the two nitrogens. Each of these structures permits two racemic diastereoisomers based on the relative position of the moiety attached to the double-bonded nitrogen, e.g., $A^1$ and $A^2$.

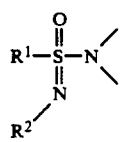

and

-continued

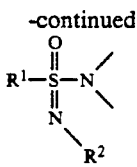

All eight possible stereoisomers are contemplated as within the scope of the instant invention, including racemic mixtures and each substantially pure stereoisomer.

As provided in the Examples, nmr spectroscopy of the compounds of the instant invention indicates that they exist primarily in the form of tautomer B above.

The compounds of formula 1 in which $R^2$ is $C(O)R^d$ and $R^3$ is hydrogen are sufficiently acidic to form salts with strong and weak bases. This invention also includes the pharmaceutically acceptable salts of those compounds of formula 1 which can form salts. Other compounds of formula 1 are weakly acidic in nature and accordingly may form salts with only strongly basic materials. Examples of bases which may be useful in forming pharmaceutically acceptable salts, include amines, alkali metal and alkaline-earth metal bases or quaternary ammonium bases.

Preferred alkali metal and alkaline-earth metal hydroxides as salt formers are the hydroxides of lithium, sodium, potassium, magnesium or calcium, in particular those of sodium and potassium.

Examples of amines suitable for forming salts are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, especially ethyl-, propyl-, diethyl- or triethylamine, but particularly isopropylamine and diethanolamine.

Examples of quaternary ammonium bases are in general the cations of haloammonium salts, for example the tetramethylammonium cation, the trimethylbenzylammonium cation, the triethylbenzylammonium cation, the tetraethylammonium cation or the trimethylethylammonium cation, but also the ammonium cation.

The compounds of the instant invention can be prepared using the reaction schemes disclosed in U.S. Pat. No. 4,666,506 of Hillemann (1987) and the article of Johnson, et al., The Journal of Organic Chemistry, 44, 2055-2060, 1979, both of which are incorporated herein by reference in their entirety. Preferred reaction schemes are set forth in reaction Scheme 1 and Scheme 2 herein below. The sulfinyl chloride of formula 2 can be conveniently prepared according to the process provided in Organic Syntheses Collection, Vol. IV, 937 (1963) incorporated herein by reference in its entirety.

The sulfinyl chloride is preferably reacted with silver cyanate to provide the isocyanate 3 ($R^1S(O)NCO$) according to the procedure of Jähnchen et al., 39 Z. Chem., 9 (1969), p. 305, incorporated herein by reference in its entirety. This can be accomplished in a solvent such as diethylether, dioxane, tetrahydrofuran, etc., using about 1.0 to 1.5 equivalents of silver cyanate at a temperature of about 0°-25° C. into which is added, normally dropwise, a solution of the sulfinyl chloride in a solvent such as diethyl ether or an alkane. After stirring at room temperature for about 1 to 24 hours, the solid silver chloride is removed by filtration to provide a solution of the isocyanate 3. This is then contacted with the arylamine to provide the intermediate product 4.

The symbol [O] refers to an oxidation reaction with preferred oxidants including chlorine, $SO_2Cl_2$, or N-chlorobenzotriazole as disclosed by Rees, et al., in Journal of the Chemical Society(C), 1474 (1969), or t-butyl hypochlorite (Johnson et al. supra) both of which are incorporated herein by reference in their entirety.

Intermediate 4 is contacted with a preferred oxidant, normally 1.0-1.2 equivalents, in a suitable solvent such as an ether or chlorinated hydrocarbon, preferably tetrahydrofuran. The resulting material is then added dropwise to excess amine to provide product 1. Intermediate 4 can also be prepared as shown in Scheme 2 using methods known in the art.

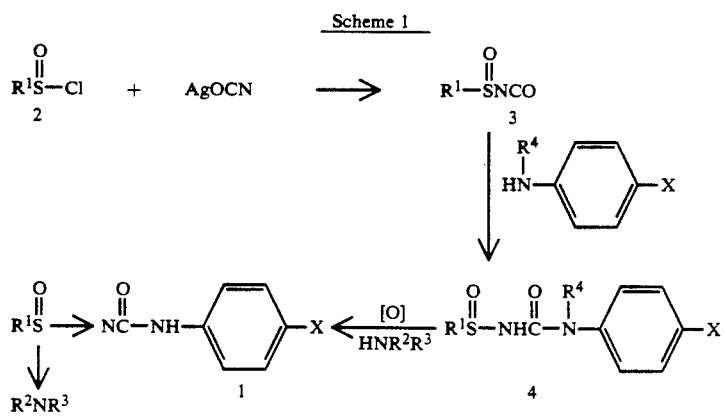

Scheme 1

Scheme 2

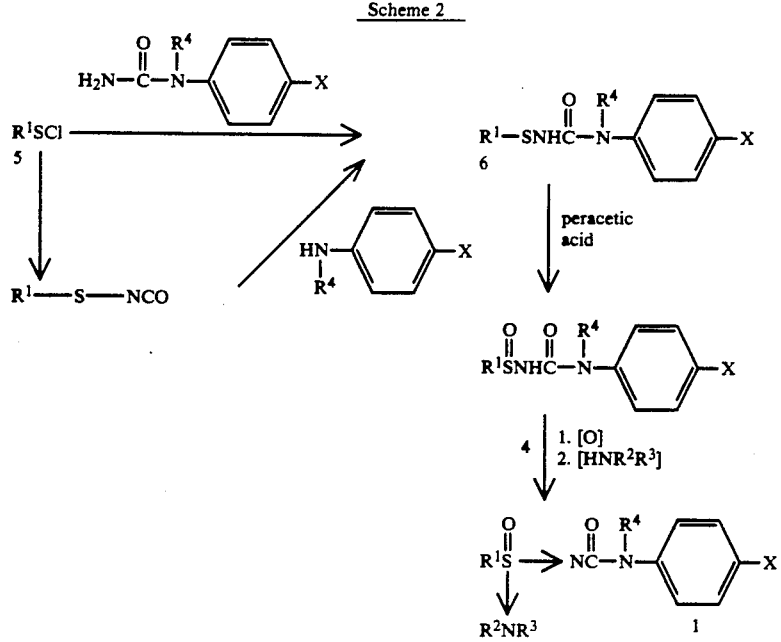

A preparation of compounds of formula 1 in which Z is ε—C(O)—N(R⁵)C(O)Rᵃ is exemplified in reaction Scheme 3. A compound of formula 1 of Scheme 1 or 2 is acylated to provide the desired product. This can be accomplished by contacting the substrate 1 with about 2.5 equivalents of a base such as triethylamine in a solvent such as dichloromethane in the presence of a catalytic amount of an acylation catalyst such as 4-dimethylaminopyridine. A typical acylating agent used in the art, for example an acid halide (R$^d$C(O)Cl shown in Scheme 3) or an acid anhydride, is added normally in the amount of about 1.0-2.5 equivalents.

Scheme 3

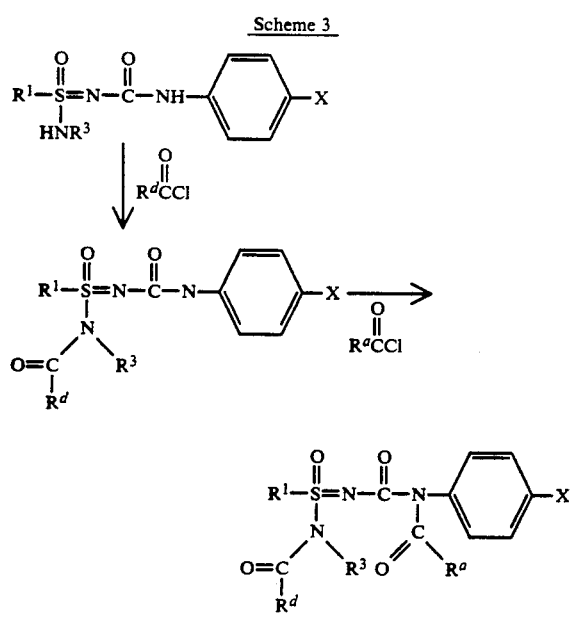

The starting materials and intermediates for the preparation of the present compounds are commercially available or can be readily prepared by the above-described methods or other methods known in the literature. References to specific literature procedures are cited in the examples and listed following the example section hereinbelow.

The following examples further illustrate the preparation of the compounds of this invention. The examples are provided for purposes of illustration only and are not to be construed as limiting the scope of the instant invention in any way.

The terms and abbreviations used in the instant examples have their normal meaning unless otherwise designed, for example, "THF" means tetrahydrofuran; "EE" refers to diethyl ether; "°C." refers to degrees celsius; "N" refers to normal or normality; "mM" refers to millimole; "g" refers to gram; "mL" means milliliter; "M" refers to molar; "NMR" refers to nuclear magnetic resonance; "m.s." refers to mass spectrometry; "EtOAc" refers to ethyl acetate; "HOAc" refers to acetic acid; "DMSO" refers to dimethylsulfoxide; "MeOH" refers to methanol; "EtOH" refers to ethanol.

Table 1 provides structures of compounds prepared in the Examples. References to literature procedures given in the Examples and are provided at the end of the Examples. Unless otherwise indicated Z in formula 1 is C(O)NR⁴R⁵, R⁴ is hydrogen, and R⁵ is p-chlorophenyl.

TABLE 1*

| Example No. | R¹ | R² | R³ |
|---|---|---|---|
| 2 | p-tolyl | H | H |
| 3 | p-tolyl | CH₃ | H |
| 4 | p-tolyl | C₂H₅ | H |
| 5 | p-tolyl | n-C₃H₇ | H |
| 6 | p-tolyl | i-C₃H₇ | H |
| 7 | p-tolyl | n-C₄H₉ | H |
| 8 | p-tolyl | i-C₄H₉ | H |
| 9 | p-tolyl | n-C₆H₁₂ | H |
| 10 | p-tolyl | C₂H₄OH | H |
| 11 | p-tolyl | C₃H₇OH | H |
| 12 | p-tolyl | CH₂C₆H₅ | H |
| 13 | p-tolyl | (CH₂)₂C₆H₅ | H |
| 14 | p-tolyl | C₆H₅ | H |
| 15 | p-tolyl | acetyl | H |
| 16 | p-tolyl | acetyl | CH₃ |

TABLE 1*-continued

| Example No. | R¹ | R² | R³ |
|---|---|---|---|
| 17 (a) | p-tolyl | acetyl | $CH_3$ |
| 18 | p-tolyl | $CH_3$ | $CH_3$ |
| 20 (b) | p-tolyl | H | H |
| 22 (c) | p-tolyl | H | H |
| 24 (d) | p-tolyl | H | H |
| 27 | p-Cl-phenyl | H | H |
| 30 | p-Br-phenyl | H | H |
| 33 | p-($C_2H_5$)phenyl | H | H |
| 36 | 3,4-($CH_3$)$_2$-phenyl | H | H |
| 39 | 3,5-($CH_3$)$_2$-phenyl | H | H |
| 45 | 3,4,5-($CH_3$)$_3$-phenyl | H | H |
| 49 | p-($CH_2OAc$)phenyl | H | H |
| 50 | p-($CH_2OH$)phenyl | H | H |
| 51 | p-(CHO)phenyl | H | H |
| 54 | 5-indanyl | H | H |
| 55 | 5-indanyl | $CH_3$ | H |
| 61 | 4-Cl-3,5-($CH_3$)$_2$-phenyl | H | H |
| 62 | 3,4-($CH_3$)$_2$phenyl | $CH_3$ | H |
| 63 | 3,4-($CH_3$)$_2$phenyl | acetyl | $CH_3$ |
| 64 | p-tolyl | $CH_2$—CH=$CH_2$ | H |
| 65 (b) | p-tolyl | $CH_3$ | H |

*Unless otherwise indicated R⁴ is hydrogen and R⁵ is p-chlorophenyl
(a) Z is —C(O)—NR⁵C(O)R$^a$ where R$^a$ is methyl
(b) R⁴ is methyl
(c) R⁵ is p-bromophenyl
(d) R⁵ is p-methylphenyl

EXAMPLE 1

N-(4-Methylbenzenesulfinyl)-N'-(4-chlorophenyl)urea

[(p-$CH_3C_6H_4$)S(O)NHC(O)NH(p-$ClC_6H_4$)]

A dry 250 mL 3-neck round-bottom flask fitted with a mechanical stirrer, addition funnel and nitrogen line was charged with silver cyanate (20.8 g, 138.6 mmol) and 70 mL of dry EE. This mixture was cooled to 0° C. and the addition funnel charged with a solution of crude p-toluenesulfinyl chloride[1] (16.95 g, 97.05 mmol) in 70 mL dry EE; the sulfinyl chloride solution was added dropwise to the cyanate mixture with vigorous stirring over 30 min. keeping the temperature at 0° C. After removing the cooling bath and stirring at room temperature for 2 h, the suspended silver chloride was removed by filtration and the yellow sulfinyl isocyanate solution was transferred to a dry 1 L 3-neck flask. A solution of p-chloroaniline (11.2 g, 87.8 mmol) in 200 mL of dry EE was added dropwise to the ice-cold sulfinyl isocyanate solution over 15 min. The product precipitated as a thick white solid during this time. After warming to room temperature and stirring overnight, the resulting solid was collected by filtration and rinsed with 1 L of EE. Vacuum drying at 40° C. for 4 h gave 20.93 g (77%) of the product as a white to light purple solid: mp=163°-164° C.; R$_f$(10/1,EtOAc/-HOAc)=0.63; ¹H NMR (300 MHz, d$_6$-DMSO) δ 2.38 (s, 3H, $CH_3$), 7.33 (d, 2H, J=8.8 Hz, Ar-H), 7.41-7.46 (m, 4H, Ar-H), 7.63 (d, 2H, J=8.1 Hz, Ar-H), 8.83 (s, 1H, exchanges with $D_2O$, NH) and 9.56 (s, 1H, exchanges with $D_2O$, SONH); ¹³C NMR (75 MHz, d$_6$-DMSO) δ 21.3, 120.8, 125.2, 127.0, 129.2, 130.2, 137.9, 141.6, 142.0 and 153.2; IR(KBr) 327.4, 3158, 1698, 1603, 1544, 1492, 1426, 1398, 1307, 1290, 1247, 1207, 1178, 1096, 1024, 1011, 901 and 824 cm⁻¹; FDMS(DMSO) m/e 308,310 (M+). Anal Calcd for $C_{14}H_{13}Cl_1N_2O_2S_1$: C, 54.46; H, 4.24; N, 9.07. Found C, 54.34; H, 4.32; N, 8.91.

EXAMPLE 2

N-[[(4-chlorophenyl)amino]carbonyl]-4-methylbenzenesulfonimidamide

[(p-$CH_3C_6H_4$)S(O)($NH_2$)NC(O)NH(p-$ClC_6H_4$)]

The product of Example 1 (1.85 g, 6.0 mmol) was suspended in 50 mL of dry THF under nitrogen and treated with N-chlorobenzotriazole[2] (968 mg, 6.3 mmol) in one portion. The mixture became homogeneous and yellow after 10 min and was stirred another 25 min. This solution was added dropwise over 10 min to 25 mL of ammonia at −78° C. After stirring 15 min the mixture was allowed to warm to RT for 2 h. The volatiles were removed under vacuum and the residue diluted with 50 mL of water. The resulting slurry of white solid, after being stirred for 15 min, was collected by filtration and rinsed with water (20 mL) and EE (50 mL). Vacuum drying overnight at 50° C. yielded 1.43 g (74%) of the product as a white solid: mp=171°-172° C.; R$_f$(1/9, MeOH/CHCl$_3$)=0.48; ¹H NMR (300 MHz, d$_6$-DMSO) δ 2.36 (s, 3H, $CH_3$), 7.18 (d, 2H, J=8.8 Hz, Ar-H), 7.37 (d, 2H, J=8.0 Hz, Ar-H), 7.45-7.48 (m, 4H, 2H exchanges with $D_2O$, 2Ar-H+$HH_2$), 7.76 (d, 2H, J=8.2 Hz, Ar-H) and 9.24 (s, 1H, exchanges with $D_2O$, NH); ¹³C NMR (75 MHz, d$_6$-DMSO) δ 21.4, 119.9, 125.2, 127.0, 128.6, 129.6, 140.2, 141.0, 142.8 and 157.2; IR(KBr) 3429, 3401, 3279, 3056, 1651, 1618, 1591, 1521, 1494, 1400, 1312, 1273, 1222, 1175, 1114, 1093, 1011, 952, 910, 830, 815, 778, 701 and 686 cm⁻¹; UV(EtOH) λ$_{max}$(e) 205.2(34293), 254.4(29327) nm; FDMS(DMSO) m/e 323,325 (M+). Anal Calcd for $C_{14}H_{14}Cl_1N_3O_2S_1$: C, 51.93; H, 4.36; N, 12.98. Found C, 51.67; H, 4.47; N, 12.68.

EXAMPLE 3

N-[[(4-Chlorophenyl)amino]carbonyl]-N',4-dimethylbenzenesulfonimidamide $CH_3C_6H_4$)S(O)(NHCH$_3$)NC(O)NH(p-ClC$_6$N$_4$)

A flame-dried, 500 mL 3-neck round-bottom flask was charged with 200 mL of dry THF and the product of Example 1 (6.48 g, 21.0 mmol). N-chlorobenzotriazole[2](3.39 g, 22.07 mmol) was added in one portion and stirring continued another 25 min. The resulting solution was added dropwise to 100 mL of methylamine at −78° C. over 10 min. The cooling bath was removed and stirred continued at room temperature for 3 h. The reaction solution was concentrated in vacuo and the resulting residue dissolved in 350 mL of EtOAc and washed with 1N HCl solution (1×100 mL), water (1×100 mL) and brine (1×100 mL). After drying (Na$_2$SO$_4$), filtration and evaporation gave a foam (10 g). Trituration with warm toluene (120 mL) followed by cooling gave a white crystalline product which was collected by filtration, rinsed with chilled toluene (20 mL) and vacuum dried to yield 3.89 g (55%) of the product: mp=79°-81° C.; R$_f$(1/9, MeOH/CHCl$_3$)=0.69; ¹H NMR (300 MHz, d$_6$-DMSO) δ 2.37 (s, 3H, $CH_3$), 2.40 (d, 3H, J=4.9 Hz, NCH$_3$), 7.20 (d, 2H, obscuring NH, 3H, J=8.8 Hz, 1H exchanges with $D_2O$, Ar-H+NH), 7.72 (d, 2H, J=8.2 Hz, Ar—H) and 9.33 (s, 1H, exchanges with $D_2O$, NH); ¹³C NMR (75 MHz, d$_6$—DMSO) δ 21.4, 28.1, 120.0, 125.4, 127.7, 128.6, 130.0, 136.3, 140.0, 143.4 and 156.8; IR(KBr) 3357, 1630, 1592, 1526, 1399, 1278, 1232, 1121, 1090, 1082, 1011, 927, 829, 774 and 687 cm⁻¹; UV(EtOH) λ$_{max}$(e) 204.6(37504), 254.6(27729) nm; FDMS (DMSO) m/e 337, 339 (M+). Anal Calcd for $C_{15}H_{16}Cl_1N_3O_2S_1$: C, 53.33; H, 4.77; N, 12.44. Found C, 53.09; H, 4.72; N, 12.26.

EXAMPLE 4

[(p-CH$_3$C$_6$H$_4$)S(O)(NHCH$_2$CH$_3$)NC(O)NH(p-ClC$_6$H$_4$)]

The method of Example 3 was followed using the product of Example 1 (6.17 g, 20.0 mmol), N-chlorobenzotriazole[2] (3.23 g, 21.0 mmol) and ethylamine (13 mL) at 5°-10° C. The crude product was chromatographed by Prep 500 (silica, toluene/EtOAc) and silica gel flash chromatography (toluene/EtOAc) to give 4.0 g of crude product. This was recrystallized from EE/hexane to yield 3.3 g (47%) of the product as a white solid.

Analysis of this product gave the following results: mp=134.5°-136° C.; R$_f$(EtOAc)=0.64; $^1$H NMR (300 MHz, d$_6$—DMSO) δ 0.98 (t, 3H, J=7.2 Hz, CH$_3$CH$_2$), 2.37 (s, 3H, CH$_3$), 2.76-2.84 (m, 2H, CH$_3$CH$_2$), 7.21 (d, 2H, J=8.8 Hz, Ar—H), 7.39 (d, 2H, J=8.1 Hz, Ar—H), 7.48 (d, 2H, J=8.8 Hz, Ar-H), 7.59 (s, 1H, exchanges with D$_2$O, HH), 7.74 (d, 2H, J=8.2 Hz, Ar—H) and 9.29 (s, 1H, exchanges with D$_2$O, NH); IR(KBr) 3282, 3242, 2979, 1644, 1593, 1530, 1400, 1275, 1227, 1134 and 1108 cm$^{-1}$; UV(EtOH) λ$_{max}$(e) 204.4(38437) and 254.8(29281) nm; FDMS (DMSO) m/e 351, 353 (M+). Anal Calcd for $C_{16}H_{18}Cl_1N_3O_2S_1$: C, 54.62; H, 5.16; N, 11.94. Found C, 54.39; H, 5.21; N, 11.65.

EXAMPLE 5

[(p-CH$_3$C$_6$H$_4$)S(O)(NHCH$_2$CH$_2$C$_3$)NC(O)NH(p-ClC$_6$H$_4$)]

The method of Example 3 was followed using the product of Example 1 (12.4 g, 40.2 mmol), N-chlorobenzotriazole[2] (6.7 g, 44 mmol) and n-propylamine (9 mL, 110 mmol) at 0° C. The crude product (16.3 g) was purified by Prep 500 (toluene/EtOAc) chromatography and recrystallized from 50 mL EE/hexane (1:1) to yield 4.04 g (27%) of the product as a white solid.

Analysis of the product gave the following results: mp=118°-119.5° C.; R$_f$(1/1, EtOAc/hexane)=0.62; $^1$H NMR (300 MHz, d$_6$-DMSO) δ 0.7-0.8 (m, 3H, CH$_2$CH$_2$CH$_3$), 1.35-1.42 (m, 2H, CH$_2$CH$_2$CH$_3$), 2.37 (s, 3H, CH$_3$), 2.68-2.74 (m, 2H, CH$_2$CH$_2$CH$_3$), 7.20 (d, 2H, J=8.8 Hz, Ar—H), 7.38 (d, 2H, J=8.1 Hz, Ar-H), 7.48 (d, 2H, J=8.8 Hz, Ar-H), 7.61 (m, 1H, exchanges with D$_2$O, NH) and 9.29 (bs, 1H, exchanges with D$_2$O, NH); IR(KBr) 3298, 3252, 2974, 1644, 1593, 1532, 1399, 1230, 1137, 1003, 836 and 681 cm$^{-1}$; UV(EtOH) λ$_{max}$(e) 206.0(33591) and 254.8 (29371) nm; FDMS (DMSO) m/e 365, 367(M+). Anal Calcd for $C_{17}H_{20}Cl_1N_3O_2S_1$: C, 55.81 H, 5.51; N, 11.49. Found C, 55.96; H, 5.64; N, 11.21.

EXAMPLE 6

[(p-CH$_3$C$_6$H$_4$)S(O)(NHCH(CH$_3$)$_2$)NC(O)NH(p-ClC$_6$H$_4$)]

The method of Example 3 was followed, using the product of Example 1 (5.0 g, 16.2 mmol), t-butylhypochlorite (2.0 mL, 16.9 mmol) and 50 mL of 2-propylamine. Silica gel flask chromatography (EtOAc/hexane) yielded 4.87 g (82%) of the product as a yellow foam.

Analysis of the product gave the following results: mp=144°-146°C.; R$_f$(1/1, EtOAc/hexane)=0.66; $^1$H NMR (300 MHz, d$_6$—DMSO) δ 0.90 (d, 3H, J=6.5 Hz, CHCH$_3$), 1.03 (d, 3H, J=6.5 Hz, CHCH$_3$), 2.36 (s, 3H, CH$_3$), 3.20-3.40 (m, 1H, CHCH$_3$), 7.20 (d, 2H, J=8.9 Hz, Ar—H), 7.38 (d, 2H, J=8.2 Hz, Ar—H), 7.48 (d, 2H, J=8.9 Hz, Ar—H), 7.63 (d, 1H, J=7.7 Hz, exchanges with D$_2$O, CHNH), 7.77 (d, 2H, J=8.2 Hz, Ar—H) and 9.24 (s, 1H, exchanges with D$_2$O, NH); IR(KBr) 3285, 2975, 1636, 1593, 1494, 1398, 1272, 1231, 1112, 1089, 1011 and 829 cm$^{-1}$; UV(EtOH) λ$_{max}$(e) 203.8(39333) and 254.4(28704) nm; FDMS (DMSO) m/e 365, 367 (M+). Anal Calcd for $C_{17}H_{20}Cl_1N_3O_2S_1$: C, 55.81; H, 5.51; N, 11.48. Found C, 55.94; H, 5.54; N, 11.20.

EXAMPLE 7

[(p-CH$_3$C$_6$H$_4$)S(O)(NHCH$_2$CH$_2$CH$_2$CH$_3$)NC(O)NH(p-ClC$_6$H$_4$)]

The method of Example 3 was followed, using the product of Example 1 (5.0 g, 16.2 mmol), t-butylhypochlorite (2.0 mL, 16.9 mmol) and 50 mL of n-butylamine. Silica gel flash chromatography (EtOAc/hexane) yielded 5.45 g (88%) of the product as a foam.

Analysis of the product gave the following results: mp=103°-105° C.; R$_f$(1/1, EtOAc/hexane)=0.83; $^1$H NMR (300 MHz, d$_6$—DMSO) δ 0.76 (t, 3H, J=7.3 Hz, CH$_2$CH$_3$), 1.15-1.27 (m, 2H, CH$_2$CH$_3$), 1.27-1.40 (m, 2H, CH$_2$CH$_2$), 2.36 (s, 3H, CH$_3$), 2.60-2.80 (m, 2H, CH$_2$CH$_2$NH), 7.20 (d, 2H, J=8.8 Hz, Ar—H), 7.38 (d, 2H, J=8.2 Hz, Ar—H), 7.48 (d, 2H, J=8.8 Hz, Ar—H), 7.60 (t, 1H, J=5.8 Hz, exchanges with D$_2$O, CH$_2$NH), 7.74 (d, 2H, J=8.2 Hz, Ar—H) and 9.30 (s, 1H, exchanges with D$_2$O, NH); IR(KBr) 3283, 2959, 1637, 1593, 1526, 1399, 1232, 1090, 812 and 684 cm$^{-1}$; UV(EtOH) λ$_{max}$(e) 204.6(37357) and 254.0(28514) nm; FDMS (DMSO) m/e 379, 381 (M+). Anal Calcd for $C_{18}H_{22}Cl_1N_3O_2S_1$: C, 56.91; H, 5.84; N, 11.06. Found C, 56.87; H, 5.92; N, 10.98

EXAMPLE 8

[(p-CH$_3$C$_6$H$_4$)S(O)(NHCH$_2$CH(CH$_3$)$_2$)NC(O)NH(p-ClC$_6$H$_4$)]

The method of Example 3 was followed, using the product of Example 1 (5.0 g, 16.2 mmol) t-butylhypochlorite (2.0 mL, 16.9 mmol) and 50 mL of isobutylamine. Silica gel flash chromatography (EtOAc/hexane) yielded 4.87 g (88%) of the product as a foam.

Analysis of the product gave the following results: mp=60°-62° C.; R$_f$ (EtOAc)=0.72; $^1$H NMR (300 MHz, d$_6$—DMSO) δ 0.77 (d, 3H, J=6.5 Hz, CHCH$_3$), 0.78 (d, 3H, J=6.5 Hz, CHCH$_3$), 1.52-1.70 (m, 1H, CH(CH$_3$)$_2$), 2.36 (s, 3H, CH$_3$), 2.40-2.57 (m, 2H, CH$_2$NH), 7.20 (d, 2H, J=8.8 Hz, Ar—H), 7.38 (d, 2H, J=8.2 Hz, Ar—H), 7.48 (d, 2H, J=8.8 Hz, Ar—H), 7.66 (t, 1H, J=6.1 Hz, exchanges with D$_2$O, CH$_2$NH), 7.74 (d, 2H, J=8.2 Hz, Ar—H) and 9.30 (s, 1H, exchanges with D$_2$O, NH ); IR(KBr) 3286, 2960, 2872, 1636, 1593, 1524, 1494, 1398, 1274, 1232 and 1122 cm$^{-1}$; UV(EtOH) λ$_{max}$(e) 204.2(39301) and 254.4(28525) nm; FDMS(DMSO) m/e 379, 381 (M+). Anal Calcd for $C_{18}H_{22}Cl_1N_3O_2S_1$: C, 56.91; H, 5.84; N, 11.06. Found C, 56.96; H, 5.88; N, 10.85.

EXAMPLE 9

[(p-CH$_3$C$_6$H$_4$)S(O)[NH(CH$_2$)$_5$CH$_3$]NC(O)NH(p-ClC$_6$H$_4$)]

The method of Example 3 was followed, using the product of Example 1 (5.0 g, 16.2 mmol), t-butylhypochlorite (2.4 mL, 20.3 mmol) and 40 mL of n-hexylamine. Silica gel flash chromatography (EtOAc/hexane) yielded 3.0 g (45%) of the product as colorless crystals.

Analysis of the product gave the following results: mp=92°-93° C.; $R_f$(⅓, EtOAc/hexane)=0.76; $^1$H NMR (300 MHz, d$_6$-DMSO) δ 0.78 (t, 3H, J=7.1 Hz, C$\overline{H_2}$CH$_3$), 1.03-1.25 (m, 6H, (CH$_2$)$_3$CH$_3$), 1.25-1.43 (m, 2H, C$\overline{H_2}$CH$_2$CH$_2$), 2.36 (s, 3H, $\overline{C}$H$_3$), 2.65-2.80 (m, 2H, C$\overline{H_2}$CH$_2$N$\overline{H}$), 7.20 (d, 2H, J=8.6 Hz, Ar—H), 7.38 (d, 2H, J=8.0 Hz, Ar—H), 7.48 (d, 2H, J=8.6 Hz, Ar—H), 7.60 (bs, 1H, exchanges with D$_2$O, CH$_2$N$\overline{H}$), 7.74 (d, 2H, J=8.0 Hz, Ar—H) and 9.29 (s, 1H, exchanges with D$_2$O, NH); IR(CHCl$_3$) 3420, 2932, 1634, 1590, 1510, 1395, 1302, 1277, 1122 and 1092 cm$^{-1}$; UV(EtOH) λ$_{max}$(e) 207.4(22570) and 254.4(24999) nm; FDMS(DMSO) m/e 407, 409 (M+). Anal Calcd for C$_{20}$H$_{26}$Cl$_1$N$_3$O$_2$S$_1$: C, 58.88; H, 6.42; N, 10.30. Found C, 58.99; H, 6.58; N, 10.13.

EXAMPLE 10

[(p-CH$_3$C$_6$H$_4$)S(O)(NHCH$_2$CH$_2$OH)NC(O)NH(p-ClC$_6$H$_4$)]

The procedure of Example 3 was followed using the product of Example 1 (3.08 g, 10.0 mmol), N-chlorobenzotriazole[2] (1.54 g, 10.0 mmol) and ethanolamine (1.95 mL, 32.3 mmol) to give 6.0 g of a foam. Purification by silica gel flash chromatography (EtOAc/hexane) followed by recrystallization from toluene gave 1.48 g (40%) of the product.

Analysis of the product gave the following results: mp=112.5°-114° C.; $R_f$(EtOAc)=0.43; $^1$H NMR (300 MHz, d$_6$—DMSO) δ 2.79-2.85 (m, 2H, C$\overline{H_2}$N), 3.32 (s, 3H, Ar—C$\overline{H_3}$), 3.35-3.41 (m, 2H, C$\overline{H_2}$O$\overline{H}$), 4.70 (t, 1H, J=5.5 Hz, exchanges with D$_2$O, CH$_2$O$\overline{H}$), 7.21 (d, 2H, J=8.8 Hz, Ar—H), 7.40 (d, 2H, J=8.1 Hz, Ar—H), 7.48 (d, 2H, J=8.8 Hz, Ar—H), 7.65 (t, 1H, J=5.9 $\overline{H}$z, exchanges with D$_2$O, CH$_2$N$\overline{H}$), 7.75 (d, 2H, J=8.1 Hz, Ar—H) and 9.33 (s, 1H, exchanges with D$_2$O, NH); IR(CHCl$_3$) 1634, 1591, 1510, 1398, 1305, 1274, 1230, 1123, 1092, 1047 and 830 cm$^{-1}$; UV(EtOH) λ$_{max}$(e) 204(38740), 223(16076), 255(28541), 311.8(629) nm; FDMS(DMSO) m/e 367, 369 (M+). Anal Calcd for C$_{16}$H$_{17}$Cl$_1$N$_3$O$_3$S$_1$: C, 52.39; H, 4.67; N, 11.45. Found C, 52.19; H, 4.86; N, 11.43.

EXAMPLE 11

](p-CH$_3$C$_6$H$_4$)S(O)(NHCH$_2$CH$_2$CH$_2$OH)NC(O)NH(p-ClC$_6$H$_4$)]

The method of Example 3 was followed, using the product of Example 1 (5.0 g, 16.2 mmol), t-butylhypochlorite (2.4 mL, 20.3 mmol) and 20 mL of n-propanolamine. Silica gel flash chromatography (EtOAc/CH$_2$Cl$_2$) yielded 1.8 g (29%) of the product as a foam.

Analysis of the product gave the following results: mp=47°-48° C.; $R_f$(4/5/1, EtOAc/hexane/MeOH)=0.48; $^1$H NMR (300 MHz, d$_6$-DMSO) δ 1.45-1.58 (m, 2H, CH$_2$C$\overline{H_2}$CH$_2$), 2.37 (s, 3H, CH$_3$), 2.70-2.83 (m, 2H, CH$_2$C$\overline{H_2}$NH), 3.34-3.40 (m, 2H, C$\overline{H_2}$CH$_2$OH), 4.43 (t, 1H, exchanges with D$_2$O, J=5.1 Hz, CH$_2$O$\overline{H}$), 7.20 (d, 2H, J=8.8 Hz, Ar—H), 7.39 (d, 2H, J=8.1 Hz, Ar—H), 7.48 (d, 2H, J=8.8 Hz, Ar—H), 7.57 (bs, 1H, exchanges with D$_2$O, CH$_2$N$\overline{H}$), 7.74 (d, 2H, J=8.2 Hz, Ar—H), and 9.30 (s, 1H, exchanges with D$_2$O, NH); IR(CHCl$_3$) 3420, 3020, 1636, 1591, 1509, 1397, 1303, 1275, 1123 and 1091 cm$^{-1}$; UV(EtOH) λ$_{max}$(e) 204.0(38517) and 254.2(27947) nm; FDMS(DMSO) m/e 381, 383 (M+). Anal Calcd for C$_{17}$H$_{20}$Cl$_1$N$_3$O$_3$S$_1$: C, 53.47; H, 5.28; N, 11.00. Found C, 53.16; H, 5.33; N, 11.06.

EXAMPLE 12

[(p-CH$_3$C$_6$H$_4$)S(O)(NHCH$_2$C$_6$H$_5$)NC(O)NH(p-ClC$_6$H$_4$)]

The method of Example 3 was followed, using the product of Example 1 (5.0 g, 16.2 mmol); t-butylhypochlorite (2.4 mL, 20.3 mmol) and 40 mL of benzylamine. Silica gel flash chromatography (EtOAc/hexane and EtOAc/CH$_2$Cl$_2$) yielded 2.9 g (43%) of the product as a foam.

Analysis of the product gave the following results: mp=49°-51° C.; $R_f$(⅓, EtOAc/hexane)=0.65; $^1$H NMR (300 MHz, d$_6$-DMSO) δ 2.37 (s, 3H, CH$_3$), 3.99 (s, 1H, ArC$\overline{H_2}$NH), 4.02 (s, 1H, ArC$\overline{H_2}$NH), 7.18-7.30 (m, 7H, Ar—$\overline{H}$), 7.38 (d, 2H, J=8.2 $\overline{H}$z, Ar—H), 7.49 (d, 2H, J=8.8 Hz, Ar—H), 7.76 (d, 2H, J=8.2 Hz, Ar—H), 8.21 (t, 1H, J=5.0 Hz, exchanges with D$_2$O, CH$_2$N$\overline{H}$), and 9.36 (s, 1H, exchanges with D$_2$O, NH); IR(KBr) 3282, 1635, 1593, 1494, 1455, 1399, 1306, 1272, 1231 and 1122 cm$^{-1}$; UV(EtOH) λ$_{max}$(e) 208.2(28851) and 253.6(28726) nm; FDMS(DMSO) m/e 413, 415 (M+). Anal Calcd for C$_{21}$N$_{20}$Cl$_1$N$_3$O$_2$S$_1$: C, 60.94; H, 4.87; N, 10.15. Found C, 61.12; H, 4.80; N, 9.87.

EXAMPLE 13

[(p-CH$_3$C$_6$H$_4$)S(O)(NHCH$_2$CH$_2$C$_6$H$_5$)NC(O)NH(p-ClC$_6$H$_4$)]

The method of Example 3 was followed, using the product of Example 1 (5.0 g, 16.2 mmol), t-butylhypochlorite (2.4 mL, 20.3 mmol) and 45 mL of phenethylamine. Crystallization from EtOAc followed by vacuum drying at 40° C. yielded 2.8 g (40%) of the product.

Analysis of the product gave the following results: mp=79°-80° C.; $R_f$(30/70, EtOAc/hexane)=0.44; $^1$H NMR (300 MHz, d$_6$-DMSO) δ 2.36 (s, 3H, CH$_3$), 2.67 (t, 2H, J=7.5 Hz, CH$_2$C$\overline{H_2}$Ar), 2.90-3.05 (m, 2H, C$\overline{H_2}$NH), 7.10-7.30 (m, 7H, Ar—H), 7.36 (d, 2H, J=8.1 Hz, Ar—H), 7.47 (d, 2H, J=8.8 Hz, Ar—H), 7.69 (d, 2H, J=8.1 Hz, Ar—H, obscurring 1H that exchanges with D$_2$O, NH), and 9.33 (s, 1H, exchanges with D$_2$O, NH); IR(CHCl$_3$) 3420, 3028, 3012, 1635, 1510, 1395, 1277, 1227, 1206 and 1092 cm$^{-1}$; UV(EtOH) λ$_{max}$(e) 204.8(44173) and 254.4 (28180) nm; FDMS(DMSO) m/e 427, 429 (M+). Anal Calcd for C$_{22}$H$_{22}$Cl$_1$N$_3$O$_2$S$_1$: C, 61.75 H, 5.18; N, 9.82. Found C, 62.00; H, 5.33; N, 9.88.

EXAMPLE 14

[(p-CH$_3$C$_6$H$_4$)S(O)(NHC$_6$H$_5$)NC(O)NH(p-ClC$_6$H$_4$)]

The method of Example 3 was followed using the product of Example 1 (6.2 g, 20 mmol), N-chlorobenzotriazole[2] (3.2 g, 21 mmol) and aniline (2.0 g, 21 mmol) to give the crude product as a foam (10.6 g). Silica gel flash chromatography (1/9, MeOH/CHCl$_3$), followed by recrystallization from 75 mL of warm toluene gave 4.8 g (59%) of the product as a white solid Analysis of the product gave the following results: mp=160°-161.5° C.; $R_f$(1/9, MeOH/CHCl$_3$)=0.77; $^1$H NMR (300 MHz, d$_6$—DMSO) δ 2.32 (s, 3H, CH$_3$), 7.00-7.26 (m, 7H, Ar—H), 7.35 (d, 2H, J=8.2 $\overline{H}$z, Ar—H), 7.53 (d, 2H, J=8.8 Hz, Ar—H), 7.75 (d, 2H, J=8.2 Hz, Ar—H), 9.46 (bs, 1H, exchanges with D$_2$O, N$\overline{H}$) and 10.30 (bs, 1H, exchanges with D$_2$O, NH); $^{13}$C NMR (75 MHz, d$_6$—DMSO) δ 21.3, 120.2, 121.1, 124.5, 125.7, 127.7, 128.8, 129.5, 130.0, 136.9, 137.9, 139.9, 143.8 and 156.2; IR(KBr) 3353, 3166, 1637, 1590, 1495, 1398, 1287, 1214, 1124 and 685 cm$^{-1}$; UV(EtOH) $\lambda_{max}$(e) 205.8(44356), 255.2(34798) nm; FDMS(DMSO) m/e 399, 401 (M+). Anal Calcd for $C_{20}H_{18}Cl_1N_3O_2S_1$: C, 60.07 H, 4.54; N, 10.51. Found C, 60.13; H, 4.53; N, 10.26.

EXAMPLE 15

[(p-CH$_3$C$_6$H$_4$)S(O)(NHC(O)CH$_3$)NC(O)NH(p-ClC$_6$H$_4$]

The method of Example 16 was followed, using the product of Example 2 (2.07 g, 6.4 mmol), Et$_3$N (1.75 mL, 12.8 mmol), DMAP (5.0 mg) and acetic anhydride (0.70 mL, 7.5 mmol) in CH$_2$Cl$_2$ (50 mL). Recrystallization from EtOAc/hexane, followed by vacuum drying at 50° C. yielded 2.0 g (85.5%) of the product.

Analysis of the product gave the following results: mp=168.5°-170° C.; R$_f$(19/1, CH$_2$Cl$_2$/MeOH)=0.08; $^1$H NMR (300 MHz d$_6$—DMSO) δ 1.93 (s, 2H, COCH$_3$), 2.38 (s, 3H, Ar—CH$_3$), 7.26 (d, 2H, J=8.8 Hz, Ar—H), 7.42 (d, 2H, J=8.2 Hz, Ar—H), 7.54 (d, 2H, J=8.8 Hz, Ar—H), 7.89 (d, 2H, J=8.3 Hz, Ar—H), 9.53 (s, 1H, exchanges with D$_2$O, NH) and 12.06 (bs, 1H, exchanges with D$_2$O, NH); IR(KBr) 3321, 3053, 2851, 1590.5, 1706, 1638, 1594, 1534, 1283, 1138, 827 and 692 cm$^{-1}$; UV(EtOH) $\lambda_{max}$(e) 204.2(37771) and 256.8(29683) nm; FDMS(DMSO) m/e 365, 367 (M+). Anal Calcd for $C_{16}H_{16}Cl_1N_3O_3S_1$: C, 52.53; H, 4.41; N, 11.49. Found C, 52.49; H, 4.49; N, 11.20.

EXAMPLE 16

](p-CH$_3$C$_6$H$_4$)S(O)(N(CH$_3$)C(O)CH$_3$)NC(O)NH(p-ClC$_6$H$_4$)]

A slurry of the product of Example 3 (5.1 g, 15.1 mmol) in 120 mL CH$_2$Cl$_2$ was prepared; to this was added Et$_3$N (4.2 mL, 30 mmol) and DMAP (30 mg, 0.25 mmol), followed by acetic anhydride (1.62 mL, 16.7 mmol) dropwise, resulting in a solution. After stirring 1 hr, the mixture was washed with 1N aqueous HCl ($\times$50 mL), water (1$\times$50 mL) and brine (1$\times$50 mL); drying (Na$_2$SO$_4$), filtration and evaporation gave 5.4 g of a white solid. Silica gel flash chromatography ($\frac{1}{2}$, EtOAc/hexane) followed by recrystallization from EtOAc/hexane yielded 2.6 g (45%) of the product.

Analysis of the product gave the following results: mp=150°-151° C.; R$_f$(1/1 EtOAc/hexanes)=0.40; $^1$H NMR (300 MHz, d$_6$—DMSO) δ 2.21 (s, 3H, Ar—CH$_3$), 2.41 (s, 3H, OAc), 3.28 (s, 3H, N—CH$_3$), 7.28 (d, 2H, J=8.7 Hz, Ar—H), 7.45 (d, 2H, J=8.1 Hz, Ar—H), 7.54 (d, 2H, J=8.7 Hz, Ar—H), 7.98 (d, 2H, J=8.1 Hz, Ar—H) and 9.74 (s, 1H, exchanges with D$_2$O, NH); IR(CHCl$_3$) 3450, 1702, 1664, 1590, 1510, 1399, 1268 and 1121 cm$^{-1}$; UV(EtOH) $\lambda_{max}$(e) 204.8(41076) and 259.0(24346) nm; FDMS(DMSO) m/e 379, 381 (M+) Anal Calcd for $C_{17}H_{18}Cl_1N_3O_3S_1$: C, 53.75; H, 4.78; N, 11.06. Found C, 53.84; H, 4.95; N, 11.05.

EXAMPLE 17

[(p-CH$_3$C$_6$H$_4$)S(O)(N(CH$_3$)C(O)CH$_3$)NC(O)N[-C(O)CH$_3$](p-ClC$_6$H$_4$)]

The method of Example 16 was followed, using the product of Example 3 (3.38 g, 10 mmol), Et$_3$N (7mL, 50 mmol), DMAP (100 mg, 0.8 mmol) and acetic anhydride (3.4 mL, 35 mmol) in 75 mL CH$_2$Cl$_2$. After stirring 48 hrs the reaction was worked up as in the example to give a yellow solid, 3.06 g. Recrystallization from 100 mL of EtOAc/hexane (3/7) yielded the product as a white solid, 2.33 g (55%).

Analysis of the product gave the following results: mp=138°-139° C.; R$_f$(1/1 EtOAc/hexane)=0.27; $^1$H NMR (300 MHz, CDCl$_3$) δ 2.30 (s, 3H, Ar—CH$_3$), 2.41 (s, 3H, OAc), 2.67 (s, 3H, OAc), 3.28 (s, 3H, N—CH$_3$), 7.17-7.22 (m, 4H, Ar—H), 7.34 (d, 2H, J=8.4 Hz, Ar—H) and 7.47 (d, 2H, J=8.6 Hz, Ar—H); IR(CHCl$_3$) 1702, 1492, 1371, 1256, 1149, 1093, 1015 and 926 cm$^{-1}$; UV(EtOH) $\lambda_{max}$(e) 203.4 (36566), 223.6(23490) and 238.6(20158) nm; FDMS(DMSO) m/e 421, 423 (M+). Anal Calcd for $C_{19}H_{20}Cl_1N_3O_4S_1$: C, 54.09; H, 4.78; N, 9.96. Found C, 54.31; H, 4.90; N, 9.91.

EXAMPLE 18

[(p-CH$_3$C$_6$H$_4$)S(O)(N(CH$_3$)$_2$)NC(O)NH(p-ClC$_6$H$_4$)]

The method of Example 3 was followed using the product of Example 1 (6.2 g, 20 mmol), N-chlorobenzotriazole[2] (3.2 g, 21 mmol) and dimethylamine (10 mL, 151 mmol) at −20° C. Recrystallization from 100 mL of warm toluene gave 4.2 g (59%) of the product.

Analysis of the product gave the following results: mp=183°-184° C.; R$_f$(1/9, MeOH/CHCl$_3$)=0.80; $^1$H NMR (300 MHz, d$_6$—DMSO) δ 2.39 (s, 3H, CH$_3$), 2.66 (s, 6H, 2CH$_3$), 7.23 (d, 2H, J=8.8 Hz, Ar—H), 7.44 (d, 2H, J=8.2 Hz, Ar—H), 7.51 (d, 2H, J=8.8 Hz, Ar—H), 7.72 (d, 2H, J=8.2 Hz, Ar—H) and 9.50 (bs, 1H, exchanges with D$_2$O, NH); IR(KBr) 3285, 1630, 1536, 1284, 1127 and 958 cm$^{-1}$; UV(EtOH) $\lambda_{max}$(e) 205.0(37973), 255.0(28328) nm; FDMS(DMSO) m/e 351, 353 (M+). Anal Calcd for $C_{16}H_{18}Cl_1N_3O_2S_1$: C, 54.62 H, 5.16; N, 11.94. Found C, 54.40; H, 4.97; N, 11.77.

EXAMPLE 19

N-(4-Methylbenzenesulfinyl)-N'-methyl-N'-(4-chlorophenyl)urea

[(p-CH$_3$C$_6$H$_4$)S(O)NHC(O)N(CH$_3$)(p-ClC$_6$H$_4$)]

The method of Example 1 was followed using p-toluenesulfinyl chloride[1] (100 mmol), silver cyanate (18.7 g, 125 mmol) and N-methyl-p-chloroaniline (12.1 mL, 100 mmol) to yield after vacuum drying at 25° C., 18.9 g (58%) of the product.

Analysis of the product gave the following results: mp=119°-121° C.; $^1$N NMR (300 MHz, d$_6$ -DMSO) δ 2.34 (s, 3H, Ar—CH$_3$), 3.19 (s, 3H, N—CH$_3$), 7.28-7.45 (m, 6H, Ar—H), 7.52 (d, 2H, J=8.1 Hz, Ar—H) and 9.78 (s, 1H, N—H); IR(KBr) 3429, 2982, 2738, 1654, 1494, 1444, 1154, 1090, 1055, 1037 and 835 cm$^{-1}$; FDMS(DMSO) m/e 322, 324 (M+). Anal Calcd for $C_{15}H_{15}Cl_1N_2O_2S_1$: C, 55.81; H, 4.68; N, 8.68. Found C, 55.61; H, 4.86; N, 8.60.

EXAMPLE 20

[(p-CH$_3$C$_6$H$_4$)S(O)(NH$_2$)NC(O)N(CH$_3$)(p-ClC$_6$H$_4$)]

The method of Example 3 was followed, using the product of Example 19 (5.0 g, 15.5 mmol), N-chlorobenzotriazole[2] (2.38 g, 15.5 mmol) and ammonia (10 mL). Silica gel flash chromatography (EtOAc/hexane) followed by recrystallization from CH$_3$Cl$_2$/hexane yielded 2.80 g (54%) of the product.

Analysis of the product gave the following results: mp=160°-161.5° C.; R$_f$(EtOAc)=0.55; $^1$H NMR (300 MHz, d$_6$—DMSO) δ 2.35 (s, 3H, CH$_3$), 3.17 (s, 3H, N—CH$_3$), 7.22-7.45 (m, 8 H, 2H exchanges with D$_2$O, Ar—H+NH$_2$) and 7.68 (d, 2H, J=8.2 Hz, Ar—H);

IR(KBr) 3316, 3163, 3038, 1614, 1493, 1423, 1361, 1255, 1205, 1034 and 1014 cm$^{-1}$; UV(EtOH) $\lambda_{max}$(e) 203.6(31100) and 233.6(16412) nm; FDMS(DMSO) m/e 337, 339 (M+). Anal Calcd for $C_{15}H_{16}C_1N_3O_2S_1$: C, 53.33; H, 4.79; N, 12.43. Found C, 53.04; H, 4.80; N, 12.41.

EXAMPLE 21

N-(4-Methylbenzenesulfinyl)-N'-(4-bromophenyl)urea

[(p-CH$_3$C$_6$H$_4$)S(O)NHC(O)NH(p-BrC$_6$H$_4$)]

The method of Example 1 was followed using p-toluenesulfinyl chloride[1] (8.6 g, 49.2 mmol), silver cyanate (9.6 g, 64 mmol) and 4-bromoaniline (10.2 g, 59 mmol) to yield after drying, 15.8 g (91%) of white product.

Analysis of the product gave the following results: mp=142°-143° C.; R$_f$(10/10/2, EtOAc//EE/HOAc)=0.75; $^1$H NMR (300 MHz, d$_6$—DMSO) $\delta$ 2.35 (s, 3H, CH$_3$), 7.34-7.44 (m, 6H, Ar—H), 7.60 (d, 2H, J=7.8 Hz, Ar—H). 8.80 (s, 1H, exchanges with D$_2$O, NH) and 9.52 (s, 1H, exchanges with D$_2$O, NH); IR(KBr) 3271, 3157, 3063, 1700, 1603, 1543, 1490, 1427, 1306, 1033, 902, 806 and 523 cm$^{-1}$. FDMS(DMSO) m/e 352,354 (M+). Anal Calcd for $C_{14}H_{13}Br_1N_2O_2S_1$: C, 47.60 H, 3.71; N, 7.93. Found C, 47.85; H, 3.69; N, 7.94.

EXAMPLE 22

[(p-CH$_3$C$_6$H$_4$)S(O)(NH$_2$)NC(O)NH(p-BrC$_6$H$_4$)]

The method of Example 2 was followed using the product of Example 21 (7.0 g, 19.8 mmol), t-butylhypochlorite (2.6 mL, 22 mmol) and ammonia (100 mL). The isolated solid (6.9 g) was recrystallized from 600 mL of toluene to give 4.05 g (55%) of the product.

Analysis of the product gave the following results: mp=171°-173° C. R$_f$(1/9, MeOH/CHCl$_3$)=0.43; $^1$N NMR (300 MHz, d$_6$—DMSO) $\delta$ 2.36 )s, 3H, CH$_3$), 7.32-7.46 (m, 8H, 2H exchanges with D$_2$O, 6Ar-H+NH$_2$), 7.76 (d, 2H, J=8.3 Hz, Ar-H) and 9.25 (s, 1H, exchanges with D$_2$O, NH); IR(KBr) 3397, 3242, 1650, 1522, 1393.8, 1270, 1236, 1125, 934, 815 and 533 cm$^{-1}$; UV(EtOH) $\lambda_{max}$(e) 256.8(29225), 204.8(34856) nm; FDMS(DMSO) m/e 367,369 (M+). Anal Calcd for $C_{14}H_{14}Br_1N_3O_2S_1$: C, 45.66; H, 3.83; N, 11.41. Found C, 45.69; H, 3.82; H, 11.50.

EXAMPLE 23

N-(4-Methylbenzenesulfinyl)-N'-(4-methylphenyl)urea

[(p-CH$_3$C$_6$H$_4$)S(O)NHC(O)NH(p-CH$_3$C$_6$H$_4$)]

The method of Example 1 was followed using p-toluenesulfinyl chloride[2] (200 mmol), silver cyanate (35.9 g, 240 mmol) and p-anisidine (21.4 g, 200 mmol) to yield after recrystallization from MeOH and vacuum drying at 25° C. 11.0 g (19%) of the product.

Analysis of the product gave the following results: mp 149°-151° C.; $^1$H NMR (300 MHz, d$_6$—DMSO) $\delta$ 2.22 (s, 3H, Ar—CH$_3$), 2.38 (s, 3H, Ar—CH$_3$), 7.08 (d, 2H, J=8.2 Hz, Ar—H), 7.28 (d, 2H, J=8.2 Hz, Ar—H), 7.42 (d, 2H, J=8.0 Hz, Ar—H), 7.62 (d, 2H, J=8.0 Hz, Ar—H), 8.57 (s, 1H, exchanges with D$_2$O, N—H) and 9.41 (s, 1H, exchanges with D$_2$O, N—H); IR(KBr) 3335, 3195, 1702, 1602, 1537, 1426, 1181, 1052, 1014, 910 and 807 cm$^{-1}$; FDMS(DMSO) m/e 288 (M+). Anal Calcd for $C_{15}H_{16}N_2O_2S_1$: C, 62.48; H, 5.59; N, 9.71. Found C, 62.47; H, 5.62; N, 9.45.

EXAMPLE 24

[(p-CH$_3$C$_6$H$_4$)S(O)(NH$_2$)NC(O)NH(p-CH$_3$C$_6$H$_4$)]

The method of Example 2 was followed, using the product of Example 23 (2.88 g, 10.0 mmol), N-chlorobenzotriazole[2] (1.53 g, 10.0 mmol) and ammonia (5 mL). Recrystallization from MeOH followed by vacuum drying at 45° C. yielded 2.09 g (69%) of the product.

Analysis of the product gave the following results: mp=172°-174° C.; R$_f$(EtOAc)=0.59; $^1$H NMR (300 MHz, d$_6$—DMSO) $\delta$ 2.16 (s, 3H, CH$_3$), 2.35 (s, 3H, CH$_3$), 6.94 (d, 2H, J=8.3 Hz, Ar—H), 7.31 (d, 2H, J=8.3 Hz, Ar—H), 7.36 (d, 2H, J=8.2 Hz, Ar—H), 7.41 (s, 2H, exchanges with D$_2$O, NH$_2$), 7.77 (d, 2H, J=8.3 Hz, Ar—H) and 8.98 (s, 1H, exchanges with D$_2$O, NH); IR(KBr) 3425, 3285, 3046, 1618, 1523, 1404, 1320, 1271, 1220, 1111, 951 and 821 cm$^{-1}$; UV(EtOH) $\lambda_{max}$(e) 207.0(28634) and 248.6(24243) nm; FDMS (DMSO) m/e 303 (M+). Anal Calcd for $C_{15}H_{17}N_3O_2S_1$: C, 59.39; H, 5.65; N, 13.85. Found C, 59.27; H, 5.63; N, 13.93.

EXAMPLE 25 p-Chlorophenylsulfinyl chloride

[(p-ClC$_6$H$_4$)S(O)(Cl]

This material was prepared quantitatively from 4-chlorothiophenol by the method of Herrmann[3] using toluene as a solvent. The crude sulfinyl chloride had the following physical properties: $^1$H NMR (300 MHz, CDCl$_3$) $\delta$ 7.36 (d, 2H, J=8 Hz, Ar—H) and 7.58 (d, 2H, J=8 Hz, Ar—H).

EXAMPLE 26

N-(4-Chlorobenzenesulfinyl)-N'-(4-chlorophenyl)urea

[(p-ClC$_6$H$_4$)S(O)NHC(O)NH(p-ClC$_6$H$_4$)]

The method of Example 1 was followed using the product of Example 25 (53.3 mmol), silver cyanate (12.33 g, 82.8 mmol) and p-chloroaniline (6.26 g, 49.1 mmol) to yield after trituration with MeOH and drying, 2.46 g (14%) of the product.

Analysis of the product gave the following results: mp 145°-146° C.; $^1$H NMR (300 MHz, d$_6$—DMSO) $\delta$ 7.34 (d, 2H, J=8.8 Hz, Ar—H), 7.45 (d, 2H, J=8.8 Hz, Ar—H), 7.68 (d, 2H, J=8.5 Hz, Ar—H), 7.77 (d, 2H, J=8.5 Hz, Ar—H), 8.91 (s, 1H, N—H), 9.79 (s, 1H, N—H); IR(CHCl$_3$) 3680, 3590, 2960, 1700, 1604, 1410, 1250 and 1034 cm$^{-1}$; FDMS(DMSO) m/e 328, 330, 332 (M+). Anal Calcd for $C_{13}H_{10}Cl_2N_2O_2S_1$: C, 47.43; H, 3.06; N, 8.51. Found C, 47.48; H, 3.13; N, 8.40.

EXAMPLE 27

[(p-ClC$_6$H$_4$)S(O)(NH$_2$)NC(O)NH(p-ClC$_6$H$_4$)]

The procedure of Example 2 was followed using the product of Example 26(2.46 g, 7.4 mmol), t-butylhypochlorite (1.03 mL, 8.6 mmol), and ammonia (50 mL) to give 1.48 g (58%) of the product.

Analysis of the product gave the following results: mp=164°-165° C.; R$_f$(1/1, EtOAc/hexane)=0.47; $^1$H NMR (300 MHz, d$_6$—DMSO) $\delta$ 7.19 (d, 2H, J=8.6 Hz, Ar—H), 7.45 (d, 2H, J=7.8 Hz, Ar—H), 7.61 (s, 2H, exchanges with D$_2$O, NH$_2$), 7.66 (d, 2H, J=7.8 Hz, Ar—H), 7.88 (d, 2H, J=8.4 Hz, Ar—H) and 9.31 (s, 1H, exchanges with D$_2$O, N—H); IR(KBr) 3426, 3280, 3031, 1621, 1510, 1401, 1271, 1239, 1222, 1097 and 830 cm$^{-1}$; UV(EtOH) $\lambda_{max}$(e) 204.0(37404), 253.0(27588) nm; FDMS(DMSO) m/e 344, 346, 348 (M+). Anal Calcd for $C_{13}H_{11}Cl_2N_3O_2S_1$: C, 45.36; H, 3.22; N, 12.21. Found C, 45.64; H, 3.43; N, 11.92.

EXAMPLE 28 p-Bromophenylsulfinyl chloride

[(p-BrC$_6$H$_4$)S(O)Cl]

This material was prepared quantitatively from 4-bromothiophenol by the method of Example 25 using toluene as a solvent. The crude sulfinyl chloride had the following physical properties: $^1$H NMR (300 MHz, CDCl$_3$) δ 7.75 (s, 4H, Ar—H).

EXAMPLE 29

N-(4-Bromobenzenesulfinyl)-N'-(4-chlorophenyl)urea

[(p-BrC$_6$H$_4$)S(O)NHC(O)NH(p-ClC$_6$H$_4$)]

The method of Example 1 was followed using the product of Example 28 (56 mmol), silver cyanate (9.25 g, 61.7 mmol) and p-chloroaniline (7.16 g, 56.1 mmol) to yield 15.6 g (75%) of the product.

Analysis of a recrystallized product (MeOH) of the product gave the following results: mp 176°–178° C.; $^1$H NMR (300 MHz, d$_6$—DMSO) δ 7.34 (d, 2H, J=8 Hz, Ar—H), 7.46 (d, 2H, J=8 Hz, Ar—H), 7.69 (d, 2H, J=8 Hz, Ar—H), 7.82 (d, 2H, J=8 Hz, Ar—H), 8.90 (s, 1H, exchanges with D$_2$O, N—H) and 9.78 (s, 1H, exchange with D$_2$O, N—H); IR(KBr) 3276, 3159, 1703, 1604, 1541, 1493, 1422, 1387, 1306, 1244, 1204, 1177, 1089, 1036, 1006 and 824 cm$^{-1}$; FDMS(DMSO) m/e 374, 376, 378 (M+). Anal Calcd for $C_{13}H_{10}Br_1Cl_1N_2O_2S_1$: C, 41.78; H, 2.70; N, 7.50. Found C, 41.82; N, 2.67; N, 7.33.

EXAMPLE 30

[(p-BrC$_6$H$_4$)S(O)(NH$_2$)NC(O)NH(p-ClC$_6$H$_4$]

The procedure of Example 2 was followed using the product of Example 29 (5.0 g 13.4 mmol), t-butylhypochlorite (2.0 mL, 14.7 mmol), and ammonia (50 mL) to give after recrystallization from ethanol, 2.47 (48%) of the product.

Analysis of the product gave the following results: mp=173°–175° C.; R$_f$(½, EtOAc/hexane)=0.64; $^1$H NMR (300 MHz, d$_6$—DMSO) δ 7.18 (d, 2H, 8.9 Hz, Ar—H), 7.45 (d, 2H, J=8.9 Hz, Ar—H), 7.61 (s, 2H, exchanges with D$_2$O, HH$_2$), 7.80 (s, 4H, Ar—H) and 9.30 (s, 1H, exchanges with D$_2$O, N—H); IR(KBr) 3401, 3242, 1649, 1592, 1574, 1522, 1399, 1267, 1235, 1009 and 833 cm$^{-1}$; UV(EtOH) $\lambda_{max}$(e) 204.8(41062), 251.8(30480) nm; FDMS(DMSO) m/e 387, 389, 391 (M+). Anal Calcd for $C_{13}H_{11}Br_1Cl_1N_3O_2S_1$: C, 40.17; H, 2.85; N, 10.81. Found C, 40.34; H, 2.79; N, 10.60.

EXAMPLE 31

4-Ethylbenzenesulfinyl chloride

]p-(CH$_3$CH$_2$)(C$_6$H$_4$)S(O)Cl]

The method of Herrmann[3] was following using 8.0 g (58 mmol) 4-ethylthiophenol.

Analysis of the product gave the following results: $^1$H NMR (300 MHz, CDCl$_3$) δ 1.31 (t, 3H, J=7.6 Hz, CH$_3$CH$_2$), 2.75 (q, 2H, J=7.6 Hz, CH$_3$CH$_2$), 7.44 (d, 2H, J=8.2 Hz, Ar—H) and 7.82 (d, 2H, J=8.2 Hz, Ar—H).

EXAMPLE 32

N-(4-Ethylbenzenesulfinyl)-N'-(4-chlorophenyl)urea

[(p-(CH$_3$CH$_2$)C$_6$H$_4$)S(O)NHC(O)NH(p-ClC$_6$H$_4$)]

The method of Example 1 was followed, using the product of Example 31 (9.2 g, 54 mmol), silver cyanate (11 g, 73 mmol) and p-chloroaniline (8.2 g, 64 mmol) to provide 51.1 g (81%) of the product.

Analysis of the product gave the following results: mp=134°–135° C.; R$_f$(10/10/2, EtOAc/EE/AcOH)=0.76; $^1$H NMR (300 MHz, d$_6$—DMSO) δ 1.19 (t, 3H, J=7.6 Hz, CH$_3$CH$_2$), 2.67 (q, 2H, J=7.6 Hz, CH$_3$CH$_2$), 7.32 (d, 2H, J=8.8 Hz, Ar—H), 7.43–7.47 (overlapping doublets, 4H, Ar—H), 7.66 (d, 2H, J=8.2 Hz, Ar—H), 8.80 (bs, 1H, exchanges with D$_2$O, NH) and 9.55 (bs, 1H, exchanges with D$_2$O, NH); IR(KBr) 3260, 3193, 2969, 2934, 1669, 1608, 1551, 1495, 1430, 1308, 1094, 1029, 832 and 653 cm$^{-1}$; FDMS(DMSO) m/e 322, 324 (M+). Anal Calcd for $C_{15}H_{15}Cl_1N_2O_2S_1$: C, 55.81; H, 4.68; N, 8.68. Found C, 56.02; H, 4.76; N, 8.74.

EXAMPLE 33

[(p-(CH$_3$CH$_2$)C$_6$H$_4$)S(O)NHC(O)NH(p-ClC$_6$H$_4$)]

The method of Example 2 was following using the product of Example 32 (9.7 g, 31 mmol). t-butylhypochlorite (4.7 mL, 39 mmol) and ammonia (50 mL) to yield after recrystallization from toluene (1250 mL) 5.88 g (58%) of the product.

Analysis of the product gave the following results: mp=168°–169° C.; R$_f$(1/9, MeOH/CHCl$_3$)=0.41; $^1$N NMR (300 MHz, d$_6$—DMSO) δ 1.16 (t, 3H, J=7.67 Hz, CH$_3$CH$_2$), 2.65 (q, 2H, J=7.6 Hz, CH$_3$CH$_2$), 7.18 (d, 2H, J=8.8 Hz, Ar—H), 7.39–7.48 (overlapping doublets obscuring bs, 6H, 2H exchanges with D$_2$O, Ar—H+NH$_2$), 7.80 (d, 2H, J=8.8 Hz, Ar—H) and 9.26 (s, 1H, exchanges with D$_2$O, NH); IR(KBr) 3389, 3258, 1647, 1591, 1524, 1493, 1399, 1234, 1124, 934 and 832 cm$^{-1}$; UV(EtOH) $\lambda_{max}$(e) 205.2(32135) and 254.6(28176) nm; FDMS (DMSO) m/e 337, 339 (M+). Anal Calcd for $C_{15}H_{16}Cl_1N_3O_2S_1$: C, 53.33; H, 4.77; N, 12.44. Found C, 53.47; H, 5.00; N, 12.43.

EXAMPLE 34

3,4-Dimethylbenzenesulfinyl chloride

[(3,4-(CH$_3$)$_2$C$_6$H$_3$)S(O)Cl]

This material was prepared quantitatively by the method of Example 25 from 3,4-dimethylthiophenol using toluene as a solvent. The crude orange product was analyzed as follows: $^1$H NMR (300 MHz, CDCl$_3$) δ 2.34 (s, 6H, 2CH$_3$), 7.37 (d, 1H, J=7.9 Hz, Ar—H), 7.62 (d, 1H, J=7.9 Hz, Ar—H), 7.67 (s, 1H, Ar—H).

EXAMPLE 35

N-(3,4-Dimethylbenzenesulfinyl)-N'-(4-chlorophenyl)urea

[(3,4-(CH$_3$)$_2$C$_6$H$_3$)S(O)NHC(O)NH(p-ClC$_6$H$_4$)]

The method of Example 1 was followed, using the product of Example 34 (6.6 g, 34.7 mmol) silver cyanate (6.8 g, 45 mmol) and p-chloroaniline (4.9 g, 38 mmol) to yield 9.14 g (82%) of the product.

Analysis of the product gave the following results: mp=129°–130° C.; R$_f$(10/10/2, EtOAc/EE/AcOH)=0.75; $^1$H NMR (300 MHz, d$_6$—DMSO) δ 2.29 (s, 3H, CH$_3$), 2.30 (s, 3H, CH$_3$), 7.32–7.51 (m, 7H, Ar—H), 8.81 (s, 1H, exchanges with D$_2$O, NH) and 9.52 (s, 1H, exchanges with D$_2$O, NH); IR(KBr) 3427, 3319, 3209, 1712, 1701, 1602, 1550, 1492, 1444, 1052, 832 and 661 cm$^{-1}$; FDMS(DMSO) m/e 322,324 (M$^+$). Anal Calcd for C$_{15}$H$_{15}$Cl$_1$N$_2$O$_2$S$_1$: C, 55.81; H, 4.68; N, 8.68. Found C, 55.53; H, 4.67; N, 8.52.

EXAMPLE 36

[3,4-(CH$_3$)$_2$C$_6$H$_3$)S(O)(NH$_2$)NC(O)NH(p-ClC$_6$H$_4$)]

The method of Example 2 was followed, using the product of Example 35 (9.14 g, 28.3 mmol), t-butylhypochlorite (4.22 mL, 35.4 mmol) and ammonia (50 mL) to yield 8.02 g (84%) of 293348. Recrystallization from toluene (500 mL) gave 6.14 g (64%) of the product as a white fluffy solid.

Analysis of the product gave the following results: mp=150°-151° C.; R$_f$(1/9, MeOH/CHCl$_3$)=0.46; $^1$H NMR (300 MHz, d$_6$—DMSO) δ 2.27 (s, 3H, CH$_3$), 2.28 (s, 3H, CH$_3$), 7.18 (d, 2H, J=8.8 Hz, Ar—H), 7.32 (d, 2H, J=8.0 Hz, Ar—H), 7.42 (s, 2H, exchanges with D$_2$O, NH$_2$), 7.47 (d, 2H, J=8.8 Hz, Ar—H), 7.60 (d, 2H, J=8.0 Hz, Ar—H), 7.65 (s, 1H, Ar—H) and 9.22 (s, 1H, exchanges with D$_2$O, NH); IR(KBr) 3299, 3189, 1629, 1589, 1523, 1399, 1279, 1232, 1126, 953, 770 and 573 cm$^{-1}$; UV(EtOH) λ$_{max}$(e) 207.0(34756) and 254.8(29008) nm; FDMS(DMSO) m/e 337, 339 (M$^+$). Anal Calcd for C$_{15}$H$_{16}$Cl$_1$N$_3$O$_2$S$_1$: C, 53.33; H, 4.77; N, 12.44. Found C, 53.58; H, 4.87; N, 12.22.

EXAMPLE 37

N-(3,5-Dimethylbenzenesulfenyl)-N'-(4-chlorophenyl)urea

[(3,5-(CH$_3$)$_2$C$_6$H$_3$)SNHC(O)NH(p-ClC$_6$H$_5$)]

The method of Example 1 was followed using 3,5-dimethylsulfenyl chloride (13.9 g, 80.7 mmol) [(prepared from 3,5-dimethylthiophenol by the procedure of Harpp, Friedlander and Smith$^4$, silver cyanate (16 g, 107 mmol)] and p-chloroaniline (12.4 g, 97.2 mmol) to give 10.8 g (46%) of crude product. Silica gel flash chromatography (EtOAc/hexane) afforded 1.92 g (8%) of the product.

Analysis of the product gave the following results: mp=180°-181° C.; R$_f$(1/9 MeOH/CHCl$_3$)=0.74; $^1$H NMR (300 MHz, d$_6$—DMSO) δ 2.22 (s, 6H, 2CH$_3$), 6.79 (s, 1H, Ar—H), 6.80 (s, 2H, Ar—H), 7.29 (d, 2H, J=8.8 Hz, Ar—H), 7.48 (d, 2H, J=8.8 Hz, Ar—H), 8.15 (s, 1H, exchanges with D$_2$O, NH) and 9.11 (s, 1H, exchanges with D$_2$O, NH); IR(KBr) 3268, 1641, 1602, 1551, 1462, 1089, 834 and 681 cm$^{-1}$; FDMS(DMSO) m/e 306,308 (M$^+$). Anal Calcd for C$_{15}$H$_{15}$Cl$_1$N$_2$O$_1$S$_1$: C, 58.72; H, 4.93; N, 9.13. Found C, 58.45; H, 5.13; N, 9.19.

EXAMPLE 38

N-(3,5-Dimethylbenzenesulfinyl)-N'-(4-chlorophenyl)urea

[(3,5-(CH$_3$)$_2$C$_6$H$_3$)S(O)NHC(O)NH(p-ClC$_6$H$_4$)]

A solution of the product of Example 37 (2.53 g, 8.7 mmol) in 50 mL THF was cooled to 0° C. Peracetic acid (32%, 1.6 mL, 8.6 mmol) was added dropwise. Two hours later additional peracetic acid (0.2 mL, 1.07 mmol) was added to complete the oxidation. After diluting the mixture with 150 mL of water and stirring for 30 min, the solid was collected by filtration and rinsed with 100 mL of water to yield, after drying, 2.16 g (81%) of product.

Analysis of the product gave the following results: mp=114°-115° C.; R$_f$(1/9 MeOH/CHCl$_3$)=0.65; $^1$H NMR (300 MHz, d$_6$—DMSO) δ 2.35 (s, 6H, 2CH$_3$), 7.23-7.46 (m, 7H, Ar—H), 8.83 (s, 1H, exchanges with D$_2$O, NH) and 9.58 (s, 1H, exchanges with D$_2$O, NH); IR(KBr) 3427, 3313, 1654, 1609, 1550, 1492, 1402, 1136, 1041, 821 and 503 cm$^{-1}$; FDMS(DMSO) m/e 322, 324 (M$^+$). Anal Calcd for C$_{15}$H$_{15}$Cl$_1$N$_2$O$_2$S$_1$: C, 55.81; H, 4.68; N, 8.68. Found C, 55.56; H, 4.65; N, 8.53.

EXAMPLE 39

[(3,5-(CH$_3$)$_2$C$_6$H$_3$)S(O)(NH$_2$)NC(O)NH(p-ClC$_6$H$_4$)]

The method of Example 2 was followed using the product of Example 38 (2.16 g, 7.04 mmol), t-butylhypochlorite (1.1 mL, 9.22 mmol) and ammonia (50 mL) to yield 1.82 g (76%) of the product.

Analysis of the product gave the following results: d$_6$—DMSO) δ 2.33 (s, 6H, 2CH$_3$), 7.18-7.23 (m, 3H, Ar—H), 7.40-7.55 (overlapping m, 6H, 2H exchanges with D$_2$O, 4Ar—H+NH$_2$) and 9.23 (s, 1H, exchanges with D$_2$O, NH); IR(KBr) 3303, 3197, 1624, 1519, 1398, 1279, 1232, 1130, 761 and 679 cm$^{-1}$; UV(EtOH) λ$_{max}$(e) 254.4(23141.2) and 206.4(33094.0) nm; FDMS(DMSO) m/e 337, 339(M$^+$). Anal Calcd for C$_{15}$H$_{16}$Cl$_1$N$_3$O$_2$S$_1$: C, 53.33; H, 4.77; N, 12.43. Found C, 53.06; H, 4.67; H, 12.23.

EXAMPLE 40

O-(3,4,5-Trimethylphenyl)-N,N-dimethylthiocarbamate

[(3,4,5-(CH$_3$)$_3$C$_6$H$_2$)OC(S)N(CH$_3$)$_2$]

A 3-neck 1000 mL round-bottom flask, fitted with a mechanical stirrer, thermometer, addition funnel and nitrogen purge, was charged with 3,4,5-trimethylphenol (35.80 g, 0.26 mol) and 200 mL of DMF. Sodium hydride (60% dispersion in mineral oil, 11.60 g, ~0.29 mol) was cautiously added in portions with vigorous stirring over 20 min. The resulting mixture was stirred 30 min under nitrogen. N,N-dimethylthiocarbamoyl chloride (39.0 g, 0.3 mol), dissolved in 30 mL of DMF, was added dropwise to the sodium trimethylphenolate mixture, maintaining an internal temperature of <60° C. After the addition was complete, the reaction mixture was heated at 90° C. for 40 min, then cooled to room temperature. Following dilution with 300 mL of cold water, the solution was poured into 350 mL of aqueous KOH, stirred briefly, and placed in the refrigerator for 2 h. The resulting solid was isolated by filtration, rinsed with 200 mL of water and dissolved with (1×100 mL), brine (1×100 mL) and dried (MgSO$_4$). Filtration and evaporation gave 62 g of crude product. Recrystallization from 100 mL of MeOH gave 35.8 g of the product as a light yellow solid (61%).

Analysis of the product gave the following results: mp=90°-91° C.; R$_f$ (3/7, EtOAc/hexane)=0.45; $^1$H NMR (300 MHz, CDCl$_3$) δ 2.16 (s, 3H, CH$_3$), 2.30 (s, 6H, 2CH$_3$), 3.33 and 3.46 (s, 6H, NCH$_3$) and 6.74 (s, 2H, Ar—H); IR(CHCl$_3$) 2983, 2871, 1535, 1479, 1398, 1304, 1276, 1217, 1179, 1121, 1026, 924 and 867 cm$^{-1}$; UV-(EtOH) λ$_{max}$(e) 205.4(25402) and 250.8(14013) nm; FDMS(DMSO) m/e 223 (M$^+$). Anal Calcd for C$_{12}$H$_{17}$N$_1$O$_1$S$_1$: C, 64.54; H, 7.67; N, 6.27. Found C, 64.77; H, 7.87; N, 6.33.

EXAMPLE 41

S-(3,4,5-Trimethylphenyl)-N,N-dimethylthiocarbamate

[(3,4,5-$(CH_3)_3C_6H_2$)SC(O)N$(CH_3)_2$]

The product of Example 40 (27.40 g, 0.12 mol) was heated neat under nitrogen to a temperature of 290° C.; rearrangement to product was conveniently monitored by TLC (30% EtOAC/hexane) and was complete after 4 h. A small sample was purified by silica gel flash chromatography (3/7, EtOAC/hexane) and recrystallized from EE/hexane to provide an analytical sample.

Analysis of the product gave the following results: mp=80°-81° C.; $R_f$ (3/7, EtOAc/hexane)=0.25; $^1$H NMR (300 MHz, $CDCl_3$) δ 2.18 (s, 3H, $CH_3$), 2.29 (s, 6H, 2$CH_3$), 3.07 (bs, 6H, N$CH_3$) and 7.16 (s, 2H, Ar—$H$); IR($CHCl_3$) 3011, 2932, 1655, 1474, 1367, 1261 and 1099 cm$^{-1}$; UV(EtOH) $\lambda_{max}$(e) 212.4(23432) nm; FDMS(DMSO) m/e 223 (M+). Anal Calcd for $C_{12}H_{17}N_1O_1S_1$: C, 64.54; H, 7.67; N, 6.27. Found C, 64.79; H, 7.71; N, 6.10.

EXAMPLE 42

3,4,5-Trimethylthiophenol

[(3,4,5-$(CH_3)_3C_6H_4$)SH]

The crude product of Example 41 (30 g, 0.13 mol) was dissolved in 350 mL of MeOH and 30 mL of water. Potassium hydroxide (35 g, 0.6 mol) was added and the mixture was heated in vacuo, the residue was diluted with water (500 mL) and washed with EE (3×100 mL). The aqueous layer was acidified with conc. HCl and extracted with $CH_2Cl_2$ (3×100 mL); the combined organic extract was dried ($Na_2SO_4$) and evaporated to yield 16.4 g of an orange oil. Vacuum distillation provided the product as a clear oil.

Analysis of the product gave the following results: bp=68°-70° C.; (0.25 mm Hg); $R_f$ (3/7, EtOAc/hexane)=0.63; $^1$H NMR (300 MHz, $CDCl_3$) δ 2.13 (s, 3H, $CH_3$), 2.25 (s, 6H, 2$CH_3$), 3.33 (s, 1H, exchanged with $D_2O$, S$H$) and 6.97 (s, 2H, Ar—$H$); IR($CHCl_3$) 3010, 2978, 1589, 1475, 1444, 1379, 1196, 886 and 853 cm$^{-1}$; UV(EtOH) $\lambda_{max}$(e) 212.0(23084) and 240.8(7803) nm; EIMS(MeOH) m/e 152(M+), 137, 119, 91. Anal Calcd for $C_9H_{12}S_1$: C, 70.99; H, 7.94. Found C, 70.89; H, 8.08.

EXAMPLE 43

3,4,5-Trimethylbernzenesulfinyl chloride

[(3,4,5-$(CH_3)_3C_6H_2$)S(O)Cl]

The method of Hermann[3] was followed using 3,4,5-trimethylthio-phenol (10 g, 66 mmol).

Analysis of the product gave the following results: $^1$H NMR (300 MHz, $CDCl_3$) δ 2.28 (s, 3H, $CH_3$), 2.40 (s, 6H, 2$CH_3$) and 7.52 (s, 2H, Ar—H).

EXAMPLE 44

N-(3,4,5-Trimethylbenzenesulfinyl)-N'-(4-chlorophenyl)urea

[(3,4,5-$(CH_3)_3C_6H_2$)S(O)NHC(O)NH(p-Cl$C_6H_4$)]

The method of Example 1 was followed, using the product of Example 43 (13.3 g, 65.7 mmol), silver cyanate (12.8 g, 85.4 mmol) and p-chloroaniline (9.2 g, 72 mmol) to provide 9.01 g (41%) of the product.

Analysis of the product gave the following results: mp=144°-145° C.; $R_f$(1/9, MeOH/$CHCl_3$)=0.66; $^1$H NMR (300 MHz, $d_6$—DMSO) δ 2.18 (s, 3H, $CH_3$), 2.31 (s, 6H, 2$CH_3$), 7.33 (d, 2H, J=8.8 Hz, Ar—$H$), 7.36 (s, 2H, Ar—$H$), 7.43 (d, 2H, J=8.8 Hz, Ar—$H$), 8.81 (bs, 1H, exchanges with $D_2O$, N$H$) and 9.50 (s, 1H, exchanges with $D_2O$, N$H$); IR(KBr) 3427, 3314, 1655, 1586, 1492, 1470, 1133, 821 and 618 cm$^{-1}$; FDMS(DMSO) m/e 336, 338 (M+). Anal Calcd for $C_{16}H_{17}Cl_1N_2O_2S_1$: C, 57.05; H, 5.09; N, 8.31. Found C, 56.75; H, 5.20; N, 8.65.

EXAMPLE 45

[(3,4,5-$(CH_3)_3C_6H_2$)S(O)($NH_2$)NC(O)NH(p-Cl$C_6H_4$)]

The method of Example 2 was followed, using the product of Example 44 (8.8 g, 26 mmol), t-butylhypochlorite (4.1 mL, 34 mmol) and ammonia (50 mL) to provide, after recrystallization from toluene (1200 mL), 5.5 g (60%) of the product as a white solid.

Analysis of the product gave the following results: mp=173°-174° C.; $R_f$(1/9, MeOH/$CHCl_3$)=0.52; $^1$H NMR (300 MHz, $d_6$—DMSO) δ 2.17 (s, 3H, $CH_3$), 2.29 (s, 6H, 2$CH_3$), 7.18 (d, 2H, J=8.8 Hz, Ar—$H$), 7.37 (s, 2H, exchanges with $D_2O$, N$H_2$), 7.46 (d, 2H, J=8.8 Hz, Ar—$H$), 7.51 (s, 2H, Ar—$H$) and 9.21 (s, 1H, exchanges with $D_2O$, N$H$); 821 and 576 cm$^{-1}$; UV(EtOH) $\lambda_{max}$(e) 206.8(43619) and 254.6(29602) nm; FDMS(DMSO) m/e 351, 353 (M+). Anal Calcd for $C_{16}H_{18}Cl_1N_3O_2S_1$: C, 54.62; H, 5.16; N, 11.94. Found C, 54.83; H, 5.22; N, 11.70.

EXAMPLE 46

4-(Acetoxymethyl)phenyl disulfide

[(p-($CH_2$OC(O)$CH_3$)$C_6H_4$)$_2$]

A solution of the 4-(hydroxymethyl)phenyl disulfide[5] (2.65 g, 9.52 mmol) in $CH_3Cl_2$ (75 mL) was treated with catalytic DMAP under nitrogen followed by $Et_3N$ (4.0 mL, 28.6 mmol) and acetic anhydride (2.24 mL, 23.8 mmol). One h later, the reaction mixture was washed with 1N HCl solution, water, brine and dried ($Na_2SO_4$); filtration followed by evaporation yielded the crude product, which was combined with a similarly prepared lot of crude product (from 1.27 g, 4.56 mmole of 4-(hydroxymethyl)phenyl disulfide) and purified by silica gel flash chromatography (EE/hexane) to provide 4.45 g (87%) of the product.

Analysis of the product gave the following results: mp=52°-54° C.; $R_f$(EtOAc)=0.69; $^1$H NMR (300 MHz, $CDCl_3$) δ 2.11 (s, 3H, CO$CH_3$), 5.08 (s, 2H, Ar$CH_2$—OAc), 7.31 (d, 2H, J=8.2 Hz, Ar—$H$) and 7.50 (d, 2H, J=8.3 Hz, Ar—$H$); IR($CHCl_3$) 3028, 3013, 1735, 1494, 1380, 1362, 1231, 1210, 1028 and 1015 cm$^{-1}$; FDMS(DMSO) 362 (M+). Anal Calcd for $C_{18}H_{18}O_4S_2$: C, 59.65; H, 5.01. Found C, 59.90; H, 5.08.

EXAMPLE 47

[(p-($CH_2$OC(O)$CH_3$)$C_6H_4$)S(O)Cl]

This material was prepared from the product of Example 46 by the method of Herrmann[6]. The crude sulfinyl chloride had the following physical properties: IR(film) 1750 and 1160 cm$^{-1}$; $^1$H NMR (300 MHz, $CDCl_3$) δ 2.16 (s, 3H, CO$CH_3$), 5.21 (s, 2H, Ar$CH_2$—OAc), 7.60 (d, 2H, J=8.2 Hz, Ar—$H$) and 7.89 (d, 2H, J=8.3 Hz, Ar—$H$).

EXAMPLE 48

[(p-(CH$_2$OC(O)CH$_3$)C$_6$H$_4$)S(O)NHC(O)NH(p-ClC$_6$H$_4$)]

The method of Example 1 was following using the product of Example 47 (22.9 mmol), silver cyanate (5.46 g, 36.4 mmol) and p-chloroaniline (2.92 g, 22.9 mmol) to yield after vacuum drying at 25° C. 6.15 g (73.4%) of the product.

Analysis of the product gave the following results: mp=131°-133° C.; $^1$H NMR (300 MHz, d$_6$—DMSO) δ 2.07 (s, 3H, CO—CH$_3$), 5.16 (s, 2H, ArCH$_2$—OAc), 7.34 (d, 2H, J=8.8 Hz, Ar—H), 7.44 (d, 2H, J=8.8 Hz, Ar—H), 7.59 (d, 2H, J=8.1 Hz, Ar—H), 7.75 (d, 2H, J=8.1 Hz, Ar—H), 8.84 (s, 1H, exchanges with D$_2$O, H—H) and 9.67 (s, 1H, exchanges with D$_2$O, N—H); IR(KBr) 3264, 3195, 3130, 1746, 1689, 1668, 1609, 1551, 1495, 1481, 1245, 1225, 1094, 1067, 1028 and 1010 cm$^{-1}$; FDMS(DMSO) m/e 366, 268(M+). Anal Calcd for C$_{16}$H$_{15}$Cl$_1$N$_2$O$_4$S$_1$: C, 52.39; H, 4.12; N, 7.64. Found C, 50.29; H, 4.17; N, 7.79.

EXAMPLE 49

[(p-(CH$_2$OC(O)CH$_3$C$_6$H$_4$)S(O)(NH$_2$)NC(O)NH(p-ClC$_6$H$_4$)]

The procedure of Example 2 was followed using the product of Example 48 (2.90 g, 7.92 mmol), N-chlorobenzo-triazole[2] (1.22 g, 7.92 mmol), and ammonia (excess) to give 2.84 g (94%) of the product; recrystallization from EtOAc and vacuum drying at 50° C. for 65 h returned 1.6 g of the product.

Analysis of the product gave the following results: mp=170°-172° C.; R$_f$ (30/19/1, Toluene/THF/HOAc,)=0.50; $^1$H NMR (300 MHz, d$_6$—DMSO) δ 2.08 (s, 3H, CO—CH$_3$), 5.14 (s, 2H, Ar—CH$_2$OAc), 7.19 (d, 2H, J=8.8 Hz, Ar—H), 7.47 (d, 2H, J=8.8 Hz, Ar—H), 7.53-7.56 (s overlapping d, 3H, 2H exchanges with D$_2$O, Ar—H and NH$_2$), 7.87 (d, 2H, J=8.4 Hz, Ar—H) and 9.28 (s, 1H, exchanges with D$_2$O, H—H); IR(KBr) 3429, 3347, 3139, 3062, 1740, 1618, 1590, 1530, 1401, 1315, 1272, 1225, 1105 and 834 cm$^{-1}$; UV(EtOH) λ$_{max}$(e) 204.8(33680), 253.6(28027) nm; FDMS(DMSO) m/e 382,384 (M+). Anal Calcd for C$_{16}$H$_{16}$Cl$_1$N$_3$O$_4$S$_1$: C, 50.33; H, 4.22; N, 11.00. Found C, 50.40; H, 4.18; N, 10.70.

EXAMPLE 50

[(p-(CH$_2$OH)C$_6$H$_4$)S(O)(NH$_2$)NC(O)NH(p-ClC$_6$H$_4$)]

A suspension of the product of Example 49 (2.95 g, 7.74 mmol) in aqueous methanol was treated with solid K$_2$CO$_3$ (1.06 g, 7.7 mmol), warmed briefly to solubilize the reactants, and stirred at room temperature for 19 h. The resulting solution was evaporated to the aqueous, diluted with brine and extracted with EtOAc (3×100 mL). The combined extract was washed with brine, dried (Na$_2$SO$_4$) and evaporated to give 1.52 g of crude product. The original aqueous layer was saturated with solid NaCl and extracted with THF/EtOAc (½, 3×150 mL). After drying (Na$_2$SO$_4$), evaporation gave an additional 1.15 g of the product. The combined crude product (2.67 g) was recrystallized from THF/hexane to give 2.19 g (83%) of product after vacuum oven drying at 60° C. for 20 h.

Analysis of the product gave the following results: mp=165°-167° C.; R$_f$(30/19/1, Toluene/THF/HOAc,)=0.26; $^1$H NMR (300 MHz, d$_6$—DMSO) δ 4.56 (d, 2H, J=5.3 Hz, Ar—CH$_2$OH), 5.37 (t, 1H, J=5.6 Hz, exchanges with D$_2$O, CH$_2$—OH), 7.19 (d, 2H, J=8.8 Hz, Ar—H), 7.45-7.50 (overlapping m, 6H, 2H exchanges with D$_2$O, Ar—H+NH$_2$), 7.85 (d, 2H, 8.2 Hz, Ar—H) and 9.25 (s, 1H, exchanges with D$_2$O, N—H); IR(KBr) 3327, 1625, 1593, 1531, 1494, 1400, 1311, 1266, 1224, 1110, 1011, 959, 828 and 782 cm$^{-1}$; UV(EtOH) λ$_{max}$(e) 204.6(34167), 253.6(28365) nm; FDMS(DMSO) m/e 340,342 (M+). Anal Calcd for C$_{14}$H$_{14}$Cl$_1$N$_3$O$_3$S$_1$: C, 49.49; H, 4.15; N, 12.37. Found C, 49.24; H, 4.01; N, 12.07.

EXAMPLE 51

[(p-(C(O)H)C$_6$H$_4$)S(O)(NH$_2$)NC(O)NH(p-ClC$_6$H$_4$)]

A solution of the product of Example 50 (2.88 g, 8.5 mmol) in THF (100 mL) was treated with MnO$_2$ (7.4 g, 84.8 mmol) under nitrogen at room temperature for 18 h. Additional MnO$_2$ (5.4 g, 62 mmol) was added and stirring continued for 48.8 h. The reaction mixture was filtered through a pad of flash silica gel (THF) and the filtrate residue, upon evaporation, purified by silica gel flash chromatography (EtOAc/hexane) to provide, after vacuum drying at 45° C., 1.40 g (49%) of the product.

Analysis of the product gave the following results: mp=137°-140° C.; R$_f$(30/19/1, Toluene/THF/HOAc,)=0.48; $^1$H NMR (300 MHz, d$_6$—DMSO) δ 7.19 (d, 2h, 8.8 Hz, Ar—H), 7.45 (d, 2H, Ar—H), 7.72 (s, 2H, exchanges with D$_2$O, NH$_2$), 8.09 (s, 4H, Ar—H), 9.35 (s, 1H, exchanges with D$_2$O, H—H) and 10.07 (s, 1H, CHO); IR(KBr) 3428, 3284, 3118, 3038, 1709, 1616, 1591, 1522, 1400, 1271, 1241, 1223, 1106, 958, 823 and 774 cm$^{-1}$; UV(EtOH) λ$_{max}$(e) 208.0(20473), 252.4(29659) nm; FDMS(DMSO) m/e 337,339 (M+). Anal Calcd for C$_{14}$H$_{12}$Cl$_1$N$_3$O$_3$S$_1$: C, 49.78; H, 3.58; N, 12.44. Found C, 50.07; H, 3.67; N, 12.16.

EXAMPLE 52

Indanesulfinic acid, sodium salt

[(5-indanyl)S(O)O$^-$Na$^+$]

Indanesulfonyl chloride[7] (10.8 g, 50 mmol) in 75 mL of acetone was treated over 10 min with a solution consisting of NaHSO$_3$ (12.6 g, 100 mmol) and NaHCO$_3$ (8.4 g, 100 mmol) in 150 mL of water. This mixture was heated at reflux (60° C.) for 1 h, during which time it became homogeneous. The cooled reaction mixture was washed with CH$_2$Cl$_2$ (1×100 mL). Evaporation of the aqueous to dryness under vacuum gave a solid residue which was extracted with CH$_3$OH (1×300 mL). This extract was filtered and evaporated to a volume of about 50 mL. The product was precipitated by the addition of 200 mL EE. Filtration and vacuum drying yielded 10.1 g (99%) of product.

Analysis of the product gave the following results: $^1$H NMR (300 MHz, D$_2$O) δ 2.05 (m, 2H, CH$_2$), 2.88 (m, 4H, 2CH$_2$), 7.4 (m, 2H, 2Ar—H) and 7.5 (s, 1H, Ar—H); FABMS (D$_2$O) m/e 227(M+), 205(M+H—Na)+.

EXAMPLE 53

N-(Indanesulfinyl)-N'-(4-chlorophenyl)urea

[(5-indanyl)S(O)NHC(O)NH(p-ClC$_6$H$_4$)]

The method of Example 1 was followed using indanesulfinyl chloride (4.2 g, 21.1 mmol) [prepared from the product of Example 52 (6.1 g, 29.9 mmol) and thionyl chloride (15 mL, 206 mmol)][1], silver cyanate (4.4 g, 29.6 mmol) and p-chloroaniline (3.5 g, 27.5 mmol) to provide 4.48 g (45%) of the product.

Analysis of the product gave the following results: mp=140°-142° C.; $R_f$(1/9, MeOH/CHCl$_3$)=0.68; $^1$H NMR (300 MHz, d$_6$—DMSO) δ 2.02-2.1 (m, 2H, CH$_2$), 2.89-2.94 (m, 4H, 2CH$_2$), 7.32-7.49 (m, 6H, Ar—H), 7.60 (s, 1H, Ar—H), 8.82 (s, 1H, exchanges with D$_2$O, NH) and 9.53 (s, 1H, exchanges with D$_2$O, NH); IR(KBr) 3425, 3313, 1655, 1547, 1492, 1401, 1089, 820 and 589 cm$^{-1}$; FDMS (DMSO) m/e 334, 336(M+). Anal Calcd for C$_{16}$H$_{15}$Cl$_1$N$_2$O$_2$S$_1$: C, 57.40 H, 4.52; N, 8.37. Found C, 57.27; H, 4.62; N, 8.10.

EXAMPLE 54

[(5-indanyl)S(O)(NH$_2$)NC(O)NH(p-ClC$_6$H$_4$)]

The method of Example 2 was followed using the product of Example 53 (6.7 g, 20 mmol). N-chlorobenzotriazole[2] (3.3 g, 21.5 mmol) and ammonia (100 mL) to give 5.89 g of the product as a tan solid. After washing with 125 mL absolute EtOH and vacuum drying, there remained 5.0 g (71%) of the product.

Analysis of the product gave the following results: mp=175°-176° C.; $R_f$(1/9, MeOH/CHCl$_3$)=0.66; $^1$H NMR (300 MHz, d$_6$—DMSO) δ 1.95-2.1 (m, 2H, CH$_2$), 2.87-2.93 (m, 4H, 2CH$_2$), 7.18 (d, 2H, J=8.8 Hz, Ar—H), 7.37-7.49 (m, 5 H, 2H exchanges with D$_2$O, 3Ar—H+NH$_2$), 7.65 (d, 1H, J=7.9 Hz, Ar—H), 7.73 (s, 1H, Ar—H) and 9.23 (bs, 1H, exchanges with D$_2$O, NH); IR(KBr) 3292, 3182, 2962, 1622, 1589, 1520, 1310, 1281, 1233, 1127, 956, 829 and 775 cm$^{-1}$; UV(EtOH) λ$_{max}$(e) 206.2(38823), 255.0(25277) nm; FDMS(DMSO) m/e 349, 351 (M+). Anal Calcd for C$_{16}$H$_{16}$Cl$_1$N$_3$O$_2$S$_1$: C, 54.93 H, 4.61; N, 12.01. Found C, 55.13; H, 4.59; N, 12.09.

EXAMPLE 55

[(5-indanyl)S(O)(NHCH$_3$)NC(O)NH(p-ClC$_6$H$_4$)]

The method of Example 3 was followed using the product of Example 53 (3.3 g, 10 mmol), N-chlorobenzotriazole[2] (1.6 g, 10.5 mmol) and methylamine (30 mL) to give 4.2 g of foam. Silica gel flash chromatography (1/19, MeOH/CHCl$_3$) followed by recrystallization from 20 mL of toluene gave 1.6 g (44%) of the product.

Analysis of the product gave the following results: mp=131°-133° C.; $R_f$(1/9, MeOH/CHCl$_3$)=0.74; $^1$H NMR (300 MHz, d$_6$—DMSO) δ 1.95-2.1 (m, 2H, CH$_2$), 2.42 (s, 3H, CH$_3$), 2.87-2.93 (m, 4H, 2CH$_2$), 7.18 (d, 2H, J=8.8 Hz, Ar—H), 7.37-7.49 (m, 4H, 1H exchanges with D$_2$O, 3Ar—H+NH), 7.65 (d, 1H, J=7.9 Hz, Ar—H), 7.73 (s, 1H, Ar—H) and 9.31 (bs, 1H, exchanges with D$_2$O, NH); IR(KBr) 3332, 3185, 1621, 1516, 1399, 1307, 1229, 1092, 1050, 935, 816 and 774 cm$^{-1}$; UV(EtOH) λ$_{max}$(e) 206.0(45381), 254.2(29481) nm; FABMS(DMSO) m/e 364, 366 (M+). Anal Calcd for C$_{17}$H$_{18}$Cl$_1$N$_3$O$_2$S$_1$: C, 56.12 H, 4.98; N, 11.55. Found C, 56.03; H, 5.01; N, 11.32.

EXAMPLE 56

O-(4-Chloro-3,5-dimethylphenyl)-N,N-dimethylthiocarbamate

[(4-Cl-3,5-(CH$_3$)$_2$C$_6$H$_2$)OC(S)N(CH$_3$)$_2$]

This material was prepared in 83% yield from 15.7 g (100 mmol) 4-chloro-3,5-dimethylphenol using the procedure of Goralski and Burk[8]. Recrystallization from EE/hexane gave an analytical sample.

Analysis of the product gave the following results: mp=125°-126° C.; $R_f$(3/7, EtOAc/hexane)=0.42; $^1$H NMR (300 MHz, CDCl$_3$) δ 2.39 (s, 6H, 2CH$_3$), 3.33 (s, 3H, NCH$_3$), 3.46 (s, 3H, NCH$_3$), 6.82 (s, 2H, Ar—H); IR(KBr) 2987, 1538, 1468, 1399, 1311, 1277, 1213, 1155, 1054 and 868 cm$^{-1}$; UV(EtOH) λ$_{max}$(e) 251.2 (13933) and 204.2 (30099) nm; FDMS(DMSO) m/e 243, 245 (M+). Anal Calcd for C$_{11}$H$_{14}$Cl$_1$N$_1$O$_1$S$_1$: C, 54.20; H, 5.79; N, 5.75. Found C, 54.45; H, 6.00; N, 5.86.

EXAMPLE 57

S-(4-Chloro-3,5-dimethylphenyl)-N,N-dimethylthiocarbamate

[(4-Cl-3,5-(CH$_3$)$_2$C$_6$H$_2$)SC(O)N(CH$_3$)$_2$]

The method of Example 41 was followed, using O-(4-chloro-3,5-dimethyl-phenyl)-N,N-dimethylthiocarbamate (18 g, 74 mmol) and heating at 210° C. for 7 h. A small sample was purified by silica gel chromatography (3/7, EtOAc/hexane) to provide an analytical sample as a yellow solid.

Analysis of the product gave the following results: mp=99°-100° C.; $R_f$(3/7 EtOAc/hexane)=0.28; $^1$H NMR (300 MHz, CDCl$_3$) δ 2.39 (s, 6H, 2CH$_3$), 3.07 (bs, 6H, 2NCH$_3$), 7.23 (s, 2H, Ar—H); IR(CHCl$_3$) 3012, 1657, 1465, 1368, 1262, 1101 and 1052 cm$^{-1}$; UV(EtOH) λ$_{max}$(e) 248.0 (8002) and 207.8 (30759) nm; FDMS(DMSO) m/e 243, 245 (M+). Anal Calcd for C$_{11}$H$_{14}$Cl$_1$N$_1$O$_1$S$_1$: C, 54.20; H, 5.79; N, 5.75. Found C, 54.47; H, 5.86; N, 6.02.

EXAMPLE 58

4-Chloro-3,5-dimethylthiophenol

[(4-Cl-3,5-(CH$_3$)$_2$C$_2$H$_2$)SH]

The method of Example 42 was followed using crude S-(4-chloro-3,5-dimethylphenyl)-N,N-dimethylthiocarbamate to give a brown oil which was vacuum distilled to yield 8.9 g (72%) of the product as a light yellow oil.

Analysis of the product gave the following results: bp=70°-72° C. (0.25 mm Hg); $R_f$(1/9 EtOAc/hexane)=0.44; $^1$H NMR (300 MHz, CDCl$_3$) δ 2.34 (s, 6H, 2CH$_3$), 3.38 (s, 1H, SH), 7.02 (s, 2H, Ar—H); IR(CHCl$_3$) 3010, 2985, 2928 1577, 1465, 1210, 1138, 1049 and 854 cm$^{-1}$; UV(EtOH) λ$_{max}$(e) 247.4 (7613) and 208.2 (15887) nm; FDMS(DMSO) m/e 342, 344 (M+). Anal Calcd for C$_8$H$_9$Cl$_1$S$_1$: C, 55.65; H, 5.25. Found C, 55.49; H, 5.32.

EXAMPLE 59

4-Chloro-3,5-Dimethylbenzenesulfinyl chloride

[(4-Cl-3,5-(CH$_3$)$_2$C$_6$H$_2$)S(O)Cl]

This material was prepared quantitatively as a bright yellow oil from the product of Example 58, following the method of Example 34.

Analysis of the crude product gave the following results: $^1$H NMR (300 MHz, CDCl$_3$) δ 2.51 (s, 6H, 2CH$_3$), 7.61 (s, 2H, Ar—H).

EXAMPLE 60

N-(4-Chloro-3,5-dimethylbenzenesulfinyl)-N'-(4-chlorophenyl)urea

[(4-Cl-3,5-(CH$_3$)$_2$C$_6$H$_2$)S(O)NHC(O)NH(p-ClC$_6$H$_4$)]

The method of Example 1 was followed, using the product of Example 59 (9.4 g, 42 mmol), silver cyanate (7.9 g, 53 mmol) and p-chloroaniline (5.8 g, 45 mmol) to provide 9.5 g (63%) of the product.

Analysis of the product gave the following results: mp 151°-152° C.; R$_f$ (10/10/2 EtOAc/EE/AcOH)=0.82; $^1$H NMR (300 MHz, d$_6$—DMSO) δ 2.42 (s, 6H, 2CH$_3$), 7.33 (d, 2H, J=8.9 Hz, Ar—H), 7.45 (d, 2H, J=8.9 Hz, Ar—H), 7.59 (s, 2H, Ar—H), 8.88 (s, 1H, exchanges with D$_2$O, N—H) and 9.72 (s, 1H, exchanges with D$_2$O, N—H); IR(KBr) 3366, 3056, 2812, 1674, 1527 and 1049 cm$^{-1}$; FDMS(DMSO) m/e 356, 357, 358 (M+). Anal Calcd for C$_{15}$H$_{14}$Cl$_2$N$_2$O$_2$S$_1$: C, 50.43; H, 3.95; N, 7.84. Found C, 50.66; H, 4.21; N, 7.61.

EXAMPLE 61

[(4-Cl-3,5-(CH$_3$)$_2$C$_6$H$_2$)S(O)(NH$_2$)NC(O)NH(p-ClC$_6$H$_4$)]

The method of Example 2 was followed, using the product of Example 60 (8.9 g, 25 mmol), t-butylhypochlorite (3.7 mL, 31 mmol) and ammonia (50 mL) to provide, after recrystallization from 1000 mL of toluene, 5.24 g (56%) of the product as a white solid.

Analysis of the product gave the following results: mp 177°-178° C.; R$_f$ (9/1 CHCl$_3$/MeOH)=0.52; $^1$H NMR (300 MHz, d$_6$—DMSO) δ 2.39 (s, 6H, 2CH$_3$), 7.18 (d, 2H, J=8.9 Hz, Ar—H), 7.45 (d, 2H, J=8.9 Hz, Ar—H), 7.52 (s, 2H, Ar—H), 7.70 (s, 2H, exchanges with D$_2$O, NH$_2$) and 9.23 (s, 1H, exchanges with D$_2$O, NH); IR(KBr) 3307, 3201, 1630, 1592, 1525, 1401, 1275, 1232, 1125, 1048, 958 and 875 cm$^{-1}$; UV(EtOH) λ$_{max}$(e) 253.0 (28581) and 206.4 (49071) nm; FDMS(DMSO) m/e 371, 373 (M+). Anal Calcd for C$_{15}$H$_{15}$Cl$_2$N$_3$O$_2$S$_1$: C, 48.4; H, 4.06; N, 11.29. Found C, 48.61; H, 4.19; N, 11.34.

EXAMPLE 62

[(3,4-(CH$_3$)$_2$C$_6$H$_3$)S(O)(NHCH$_3$)NC(O)NH(p-ClC$_6$H$_4$)]

The method of Example 3 was followed, using the product of Example 35 (11.3 g, 35 mmol), t-butylhypochlorite (5.22 mL, 43.7 mmol) and methylamine (40 mL) to provide 11.3 g (92%) of product.

Analysis of the product gave the following results: mp 76°-79° C.; R$_f$ (9/1 CHCl$_3$/MeOH)=0.64; $^1$H NMR (300 MHz, d$_6$—DMSO) δ 2.29 (s, 6H, 2CH$_3$), 2.40 (d, 3H, J=5 Hz, NCH$_3$), 3.58 (m, 1H, exchanges with D$_2$O, HNCH$_3$), 7.20 (d, 2H, J=8.9 Hz, Ar—H), 7.36 (d, 1H, J=8 Hz, Ar—H), 7.42-7.58 (m, 4H, Ar—H), 7.61 (s, 1H, Ar—H) and 9.30 (s, 1H, exchanges with D$_2$O, N—H); IR(KBr) 3250, 1631, 1591, 1493, 1397, 1271, 1236, 1009 and 830 cm$^{-1}$; UV(EtOH) λ$_{max}$(e) 254.2 (27145) and 205.4 (38773) nm; FDMS(DMSO) m/e 351, 353 (M+). Anal Calcd for C$_{16}$H$_{18}$Cl$_1$N$_3$O$_2$S$_1$: C, 54.62; H, 5.16; N, 11.94. Found C, 54.64; H, 5.37; N, 11.72.

EXAMPLE 63

[(3,4-(CH$_3$)$_2$C$_6$H$_3$)S(O)(N(CH$_3$)C(O)CH$_3$)NC(O)NH(p-ClC$_6$H$_4$)]

The method of Example 16 was followed, using the product of Example 62 (5.3 g, 15 mmol), Et$_3$N (4.2 mL, 30 mmol), DMAP (20 mg, 0.2 mmol) and Ac$_2$O (1.8 mL, 18 mmol) to give, after trituration with EE, 3.3 g (55%) of product as a white solid.

Analysis of the product gave the following results: mp 147°-149° C.; R$_f$ (1/1 EtOAc/hexane)=0.33; $^1$H NMR (300 MHz, d$_6$—DMSO) δ 2.22 (s, 3H, CH$_3$), 2.31 (s, 3H, CH$_3$), 3.26 (s, 3H, CH$_3$), 3.31 (s, 3H, CH$_3$), 7.20 (d, 2H, J=8.9 Hz, Ar—H), 7.36 (d, 1H, J=8 Hz, Ar—H), 7.42-7.58 (m, 4H, Ar—H), 7.61 (s, 1H, Ar—H) and 9.27 (s, 1H, exchanges with D$_2$O, NH); IR(KBr) 3304, 1709, 1643, 1537, 1399, 1239, 1088 and 850 cm$^{-1}$; UV(EtOH) λ$_{max}$(e) 244.6 (21307) and 205.4 (43504) nm; FDMS(DMSO) m/e 393, 395 (M+). Anal Calcd for C$_{18}$H$_{20}$Cl$_1$N$_3$O$_3$S$_1$: C, 54.89; H, 5.12; N, 10.67. Found C, 54.88; H, 5.16; N, 10.38.

EXAMPLE 64

[(p-CH$_3$C$_6$H$_4$)S(O)(NHCH$_2$CH=CH$_2$)NC(O)NH(p-ClC$_6$H$_4$)]

The method of Example 3 was followed, using the product of Example 19 (6.45 g, 20.0 mmol), t-butylhypochlorite (2.4 mL, 20 mmol) and 30 mL of methylamine. Recrystallization from toluene gave 4.56 g (65%) product as a white solid.

Analysis of the product gave the following results: mp=119°-120° C.; R$_f$(EtOAc)=0.53; $^1$H NMR (300 MHz, d$_6$—DMSO) δ 2.31 (d, 3H, J=4.7 Hz, N—CH$_3$), 2.36 (s, 3H, CH$_3$), 3.18 (s, 3H, N—CH$_3$), 7.29-7.38 (m, 7H, 1H exchanges with D$_2$O, Ar—H+NH) and 7.61 (d, 2H, J=8.2 Hz, Ar—H); IR(KBr) 3151, 1589, 1494, 1435, 1360, 1314, 1295, 1252, 1198, 1071 and 1010 cm$^{-1}$; UV(EtOH) λ$_{max}$(e) 203.8(32668) and 235.4(17590) nm; FDMS(DMSO) m/e 351, 353 (M+). Anal Calcd for C$_{16}$H$_{18}$Cl$_1$N$_3$O$_2$S$_1$: C, 54.62; H, 5.16; N, 11.94. Found C, 54.41; H, 5.09; N, 11.90.

References

1) Kurzer, F., *Org. Syn.*, Coll. Vol. IV, 1963, 937.
2) Rees, C. W., Storr, R. C., *J. Chem. Soc. (C)*, 1969, 1474.
3) Herrmann, R., Youn, J-H, *Synthesis*, 1987, 72.
4) Harpp, D. N., Friedlander, B. T., Smith, R. A., *Synthesis*, 1979, 181.
5) Young, R. N., Gauthier, J. Y., Combs, W., *Tetrahedron Letters*, 1984, 25, 1753; Griece, R., Owen, L. N., *J. Chem. Soc.*, 1963, 1947.
6. Herrmann, R., Youn, J-H., *Tetrahedron Lett.*, 1986, 27(13), 1493.
7) Tao, E. V., Aikens, J., *Eur. Pat. Appl.*, EP 254,577.
8) Goralski, Christian T. and Burk, George A., *J. Chem. Eng. Data.*, 1975, 20(4), 443.

The compounds of formula 1 have been shown to be active against transplanted mouse tumors in vivo. The compounds were tested in C3H mice bearing a 6C3HED lymphosarcoma, also known as the Gardner lymphosarcoma (GLS), and in a variety of human tumor xenografts in CD1 nu/nu mice, including CX-1, LX-1, HXGC3, and VRC5. The 6C3HED lymphosarcoma was obtained from the Division of Cancer Treatment, National Center Institute, Tumor Bank, maintained at E. G. and G. Mason Research (Worcester, Mass.). The CX-1 human colon carcinoma and the LX-1 human lung carcinoma xenografts were obtained from the National Cancer Institute. The HXGC3 and VRC5 human colon xenografts were obtained from Dr. P. J. Houghton, St. Jude Children's Hospital in Memphis (see *Br. J. Cancer*, 37, 213 (1978)). First passage tumor was stored in liquid nitrogen using standard techniques. The transplanted tumor was reestablished from the Tumor Bank every six months or as needed. The tumor was maintained by serial passage twice weekly in C3H mice.

In the procedure the tumor was removed from passage animals and minced into 1- to 3-mm square fragments using sterile techniques. Tumor pieces were checked for sterility using both Antibiotic Medium 1 and Brain Heart Infusion (Difco, Detroit, Mich.). Recipient mice were shaved and tumor pieces were implanted subcutaneously in the auxiliary region by trocar. Drug therapy on the appropriate schedule was initiated on the day after tumor implant for 6C3HED and after a seven (7) day delay for xenografts (or other delay as noted in Table 2). The compound being tested was mixed with 2.5% Emulphor EL620 from GAF Corporation (1:40 dilution in saline). Food and water were provided ad libitium. The drug was administered orally in 0.5 ml of 2.5% Emulphor (unless otherwise indicated). The tumor was measured the day after treatment ended with two dimensional measurements (width and length) of the tumor taken using automated digital calipers interfaced to a microcomputer. Approximate weight for the tumor was calculated using the following formula [Worzalla, J. F., et al., *Invest. New Drugs*, 8, 241 (1990], (tumor weight in mg)=(width in mm)$^2$×(length in mm)/2.

At least one control group of an equal number of mice was treated with the same volume of 2.5% Emulphor only. The percent inhibition was determined by subtracting the ratio of the mean tumor size of the test group relative to the control group from one and multiplying the result times 100.

The results of several experiments in mice bearing a 6C3HED lymphosarcoma (or other tumor where indicated) when the indicated compounds were administered are provided in Table 2. In Table 2, column 1 gives the Example number of the compound used, column 2 lists the dose level in mg/kg, column 3 provides the percent inhibition of tumor growth, column 4 gives the number of mice which died relative to the total number of animals in the group, column 5 gives the method of administration of the compound, and column 6 gives the dosage schedule. The protocol used with other tumors was the same as with the 6C3HED lymphosarcoma.

TABLE 2

| Ex. No. | | Dose mg/kg | % Inhib. | Tox/ Tot | Admin (a) | Dose (b) Sched. |
|---|---|---|---|---|---|---|
| 2 | | 300.00 | 98 | 6/10 | IP | DX 8 |
| | | 150.00 | 92 | 1/10 | IP | |
| | | 25.00 | 52 | 1/10 | IV | |
| | | 12.50 | 36 | 0/10 | IV | |
| | | 800.00 | 99 | 1/10 | | BIDX 8 |
| | | 400.00 | 99 | 0/10 | | |
| | | 200.00 | 98 | 0/10 | | |
| | | 100.00 | 96 | 0/10 | | |
| | | 50.00 | 95 | 0/10 | | |
| | | 300.00 | 82 | 0/10 | | DX 8 |
| | | 150.00 | 74 | 0/10 | | |
| | | 1200.00 | 100 | 0/10 | | |
| | | 600.00 | 99 | 0/10 | | |
| | | 300.00 | 95 | 0/10 | | |
| | | 150.00 | 93 | 0/10 | | |
| | | 75.00 | 76 | 0/10 | | |
| | (c) | 500.00 | TOX | 9/9 | | BIDX 14; (b-1) |
| | (c) | 250.00 | 68 | 2/9 | | |
| | (d) | 300.00 | 66 | 5/10 | | BIDX 14; (b-2) |
| | (d) | 100.00 | 51 | 0/10 | | |
| 2 | (d) | 30.00 | 28 | 0/10 | | |
| | (d) | 10.00 | 18 | 0/10 | | |
| | (d) | 3.00 | 24 | 0/10 | | |
| 3 | | 200.00 | 100 | 0/10 | | BIDX 8 |
| | | 100.00 | 99 | 0/10 | | |
| | | 50.00 | 91 | 0/10 | | |
| | | 25.00 | 82 | 0/10 | | |
| | | 12.50 | 58 | 0/10 | | |
| | | 300.00 | 99 | 0/10 | | DX8 |
| | | 150.00 | 93 | 1/10 | | |

TABLE 2-continued

| Ex. No. | | Dose mg/kg | % Inhib. | Tox/ Tot | Admin (a) | Dose (b) Sched. |
|---|---|---|---|---|---|---|
| | | 1200.00 | TOX | 10/10 | | |
| | | 600.00 | 100 | 4/10 | | |
| | | 300.00 | 99 | 0/10 | | |
| | | 150.00 | 96 | 1/10 | | |
| | | 75.00 | 81 | 0/10 | | |
| | (d) | 300.00 | TOX | 8/8 | | BIDX 10 |
| | (d) | 150.00 | TOX | 8/8 | | |
| 4 | | 300.00 | 18 | 0/10 | IP | DX 8 |
| | | 150.00 | 10 | 0/10 | IP | |
| | | 300.00 | 96 | 0/10 | | BIDX 8 |
| | | 150.00 | 87 | 0/10 | | |
| 5 | | 300.00 | 44 | 0/10 | IP | DX 8 |
| | | 150.00 | 34 | 0/10 | IP | |
| | | 300.00 | 69 | 0/10 | | |
| | | 150.00 | 64 | 0/10 | | |
| 6 | | 150.00 | 93 | 0/10 | | BIDX 8 |
| | | 75.00 | 86 | 0/10 | | |
| | | 37.50 | 60 | 0/10 | | |
| | | 18.75 | 18 | 0/10 | | |
| | | 300.00 | 99 | 2/10 | | |
| | | 150.00 | 99 | 2/10 | | |
| 7 | | 150.00 | 88 | 0/10 | | BIDX 10 |
| | | 75.00 | 69 | 0/10 | | |
| | | 37.50 | 45 | 0/10 | | |
| | | 18.75 | 21 | 0/10 | | |
| | (e) | 50.00 | 0 | 0/10 | | BIDX 10 |
| 8 | | 150.00 | 97 | 0/9 | | BIDX 8 |
| | | 75.00 | 85 | 0/10 | | |
| | | 37.50 | 60 | 0/10 | | |
| | | 18.75 | 29 | 0/10 | | |
| | | 300.00 | TOX | 10/10 | | |
| | | 150.00 | 98 | 4/10 | | |
| | | 100.00 | 51 | 0/10 | | DX 8 |
| | | 50.00 | 31 | 0/10 | | |
| | | 25.00 | 28 | 0/10 | | |
| 9 | | 300.00 | 79 | 2/10 | | BIDX 8 |
| | | 150.00 | 65 | 0/10 | | |
| 10 | | 300.00 | 60 | 0/10 | | DX 8 |
| | | 150.00 | 40 | 0/10 | | |
| 11 | | 300.00 | 89 | 2/10 | | BIDX 8 |
| | | 150.00 | 65 | 0/10 | | |
| 12 | | 300.00 | 87 | 1/10 | | BIDX 8 |
| | | 150.00 | 73 | 0/9 | | |
| 13 | | 300.00 | 48 | 0/10 | | BIDX 8 |
| | | 150.00 | 39 | 0/10 | | |
| 14 | | 300.00 | 38 | 3/10 | IP | DX 8 |
| | | 150.00 | 1 | 2/10 | IP | |
| | | 300.00 | 5 | 0/10 | | |
| | | 150.00 | 0 | 0/10 | | |
| 15 | | 300.00 | TOX | 10/10 | IP | DX 8 |
| | | 150.00 | 0 | 0/10 | IP | |
| | | 300.00 | 84 | 0/10 | | BIDX 8 |
| | | 150.00 | 0 | 0/10 | | |
| | | 300.00 | 44 | 0/10 | | DX 8 |
| | | 150.00 | 23 | 0/10 | | |
| 16 | | 300.00 | 99 | 1/10 | | BIDX 8 |
| | | 150.00 | 98 | 1/10 | | |
| 17 | | 300.00 | 96 | 0/10 | | BIDX 8 |
| | | 150.00 | 83 | 0/10 | | |
| 18 | | 600.00 | 99 | 6/8 | IP | DX 8 |
| | | 300.00 | 93 | 4/8 | IP | |
| | | 300.00 | 63 | 0/10 | | |
| | | 150.00 | 45 | 0/10 | | |
| 20 | | 300.00 | 93 | 0/10 | | BIDX 8 |
| | | 150.00 | 83 | 0/10 | | |
| 22 | | 300.00 | 100 | 3/10 | | BIDX 8 |
| | | 150.00 | 100 | 0/10 | | |
| 24 | | 300.00 | 52 | 0/10 | IP | DX 8 |
| | | 150.00 | 31 | 0/10 | IP | |
| | | 300.00 | 40 | 0/10 | | |
| | | 150.00 | 10 | 0/10 | | |
| 27 | | 200.00 | TOX | 10/10 | | BIDX 8 |
| | | 100.00 | 100 | 9/10 | | |
| | | 100.00 | 94 | 0/10 | | |
| | | 50.00 | 80 | 0/10 | | |
| | | 25.00 | 39 | 0/10 | | |
| 30 | | 300.00 | TOX | 10/10 | | BIDX 8 |
| | | 150.00 | 99 | 3/10 | | |
| | | 150.00 | 89 | 1/10 | | |
| | | 75.00 | 67 | 0/10 | | |

TABLE 2-continued

| Ex. No. | | Dose mg/kg | % Inhib. | Tox/Tot | Admin (a) | Dose (b) Sched. |
|---|---|---|---|---|---|---|
| | | 37.50 | 42 | 1/10 | | |
| | | 18.75 | 19 | 1/10 | | |
| | | 9.00 | 4 | 0/10 | | |
| | | 50.00 | 55 | 0/10 | | |
| 33 | | 300.00 | 100 | 8/10 | | BIDX 8 |
| | | 150.00 | 100 | 8/10 | | |
| | | 100.00 | 99 | 0/10 | | |
| | | 50.00 | 98 | 1/10 | | |
| | | 25.00 | 91 | 2/10 | | |
| | | 12.50 | 60 | 0/9 | | |
| | | 6.25 | 36 | 0/10 | | |
| 36 | | 100.00 | 100 | 3/10 | IP | Days 1, 3, 5, 7 |
| | | 50.00 | 99 | 0/10 | IP | |
| | | 25.00 | 99 | 0/10 | IP | |
| | | 12.50 | 88 | 0/10 | IP | |
| | | 4.00 | 97 | 0/10 | IP | BIDX 8 |
| | | 2.00 | 75 | 0/10 | IP | |
| | | 1.00 | 43 | 0/10 | IP | |
| | | 0.50 | 29 | 0/10 | IP | |
| | | 0.25 | 16 | 0/10 | IP | |
| | | 50.00 | 100 | 6/10 | IP | DX 8 |
| | | 25.00 | 100 | 2/10 | IP | |
| | | 12.50 | 98 | 1/10 | IP | |
| | | 6.25 | 93 | 0/10 | IP | |
| | | 3.125 | 74 | 0/10 | IP | |
| 36 | | 300.00 | TOX | 10/10 | | BIDX 8 |
| | | 150.00 | 99 | 6/10 | | |
| | | 100.00 | TOX | 8/8 | | |
| | | 50.00 | 100 | 7/8 | | |
| | | 25.00 | 100 | 2/8 | | |
| | | 12.50 | 100 | 5/8 | | |
| | | 6.25 | 100 | 2/8 | | |
| | (f) | 30.00 | 9 | 0/10 | IP | DX 10 |
| | (f) | 15.00 | 0 | 0/10 | IP | |
| | (f) | 7.50 | 0 | 0/10 | IP | |
| | (f) | 3.75 | 0 | 0/10 | IP | |
| | (g) | 30.00 | TOX | 10/10 | IP | |
| | (g) | 15.00 | 74 | 6/10 | IP | |
| | (g) | 7.50 | 69 | 0/10 | IP | |
| | (g) | 3.75 | 38 | 1/10 | IP | |
| | (h) | 30.00 | 72 | 0/10 | IP | |
| | (h) | 15.00 | 42 | 0/10 | IP | |
| | (h) | 7.50 | 1 | 0/10 | IP | |
| | (h) | 3.75 | 26 | 0/10 | IP | |
| | (i) | 30.00 | 26 | 0/10 | IP | |
| | (i) | 15.00 | 6 | 0/10 | IP | |
| | (i) | 7.50 | 14 | 0/10 | IP | |
| | (i) | 3.75 | 5 | 0/10 | IP | |
| 36 | (j) | 30.00 | 23 | 4/10 | IP | DX 10, (b-2) |
| | (j) | 15.00 | 32 | 1/10 | IP | |
| | (j) | 7.50 | 10 | 0/10 | IP | |
| | (j) | 3.75 | 4 | 0/10 | IP | |
| | (k) | 30.00 | TOX | 10/10 | IP | DX 10 |
| | (k) | 15.00 | 3 | 0/10 | IP | |
| | (k) | 7.50 | 0 | 0/10 | IP | |
| | (d) | 3.75 | 0 | 0/10 | IP | |
| | (l) | 30.00 | 12 | 9/10 | IP | |
| | (l) | 15.00 | 13 | 1/10 | IP | |
| | (l) | 7.50 | 17 | 0/10 | IP | |
| | (l) | 3.75 | 6 | 0/10 | IP | |
| | (c) | 60.00 | TOX | 10/10 | IP | |
| | (c) | 30.00 | 46 | 6/10 | IP | |
| | (c) | 15.00 | 24 | 0/10 | IP | |
| | (c) | 7.50 | 1 | 0/10 | IP | |
| | (m) | 30.00 | 34 | 0/10 | IP | |
| | (m) | 15.00 | 32 | 0/10 | IP | |
| | (m) | 7.50 | 6 | 0/10 | IP | |
| 36 | (d) | 30.00 | TOX | 10/10 | IP | DX 10; (b-2) |
| | (d) | 15.00 | 18 | 1/10 | IP | |
| | (d) | 7.50 | 1 | 0/10 | IP | |
| | (d) | 3.75 | 16 | 0/10 | IP | |
| | (n) | 30.00 | 38 | 1/10 | IP | DX 10; (b-3) |
| | (n) | 15.00 | 47 | 0/10 | IP | |
| | (n) | 7.50 | 19 | 0/10 | IP | |
| | (n) | 3.75 | 10 | 0/10 | IP | |
| | (o) | 30.00 | 12 | 4/10 | IP | DX 10 |
| | (o) | 15.00 | 0 | 0/10 | IP | |
| | (o) | 7.50 | 0 | 0/10 | IP | |
| | (o) | 3.75 | 5 | 0/10 | IP | |
| | (e) | 60.00 | TOX | 10/10 | IP | DX 10; (b-2) |
| | (e) | 30.00 | 44 | 4/10 | IP | |
| | (e) | 15.00 | 0 | 0/10 | IP | |
| | (e) | 7.50 | 0 | 1/10 | IP | |
| | (e) | 20.00 | 45 | 2/9 | | DX 10 |
| | (e) | 10.00 | 10 | 0/10 | | |
| | (e) | 5.00 | 0 | 0/10 | | |
| | (p) | 30.00 | 97 | 3/10 | IP | |
| | (p) | 15.00 | 88 | 4/10 | IP | |
| | (p) | 7.50 | 63 | 1/10 | IP | |
| | (p) | 3.75 | 35 | 0/10 | IP | |
| 39 | | 200.00 | 77 | 0/10 | | BIDX 8 |
| | | 100.00 | 44 | 0/10 | | |
| 45 | | 300.00 | 100 | 3/10 | | DAYS 1, 3, 5, 7 |
| | | 150.00 | 100 | 2/10 | | |
| | | 150.00 | 99 | 2/10 | | |
| | | 75.00 | 99 | 1/10 | | |
| | | 37.50 | 99 | 2/10 | | |
| | | 18.75 | 95 | 0/10 | | |
| | | 9.37 | 78 | 0/10 | | |
| | (d) | 300.00 | 31 | 0/10 | | DAYS 1, 4, 7, 10; (b-2) |
| | (d) | 150.00 | 40 | 0/9 | | |
| 49 | | 300.00 | TOX | 10/10 | IP | DX 8 |
| | | 150.00 | 99 | 8/10 | IP | |
| | | 50.00 | 63 | 1/10 | IP | |
| | | 25.00 | 36 | 0/10 | IP | |
| | | 12.50 | 29 | 0/10 | IP | |
| | | 300.00 | 100 | 3/10 | | BIDX 8 |
| | | 150.00 | 99 | 0/10 | | |
| | | 75.00 | 96 | 0/10 | | |
| | | 50.00 | 87 | 0/10 | | |
| | | 25.00 | 64 | 0/10 | | |
| 50 | | 40.00 | 86 | 1/10 | IP | BIDX 8 |
| | | 20.00 | 72 | 0/10 | IP | |
| | | 10.00 | 49 | 0/10 | IP | |
| | | 5.00 | 34 | 0/10 | IP | |
| | | 300.00 | 100 | 9/10 | IP | |
| | | 150.00 | 99 | 0/10 | IP | |
| | | 75.00 | 96 | 0/10 | IP | |
| | | 300.00 | 99 | 1/10 | IP | DX 8 |
| | | 150.00 | 93 | 0/10 | IP | |
| | | 300.00 | 100 | 9/10 | | BIDX 8 |
| | | 150.00 | 100 | 2/10 | | |
| | | 75.00 | 99 | 2/9 | | |
| | (c) | 150.00 | 23 | 2/9 | | BIDX 10 |
| | (c) | 75.00 | 46 | 0/9 | | |
| | (c) | 40.00 | 71 | 1/10 | IP 0.6 ML | BIDX 14 |
| | (c) | 20.00 | 33 | 0/10 | IP 0.6 ML | |
| | (c) | 10.00 | 31 | 0/10 | IP 0.6 ML | |
| | (c) | 5.00 | 6 | 0/10 | IP 0.6 ML | |
| | (d) | 300.00 | 34 | 0/10 | | DX 10; (b-2) |
| | (d) | 150.00 | 32 | 0/10 | | |
| | (e) | 300.00 | 59 | 0/10 | | DX 10 |
| | (e) | 150.00 | 27 | 0/10 | | |
| 51 | | 300.00 | 99 | 9/10 | IP | DX 8 |
| | | 150.00 | 80 | 0/10 | IP | |
| 54 | | 100.00 | 70 | 0/10 | IP | BIDX 8 |
| | | 50.00 | 44 | 0/10 | IP | |
| | | 25.00 | 30 | 0/10 | IP | |
| | | 12.50 | 6 | 0/10 | IP | |
| | | 300.00 | 94 | 3/10 | IP | DX 8 |
| | | 150.00 | 86 | 1/10 | IP | |
| | | 25.00 | 19 | 0/10 | IV | |
| | | 12.50 | 3 | 0/10 | IV | |
| | | 300.00 | 33 | 0/10 | | BIDX 8 |
| | | 150.00 | 22 | 0/10 | | |
| | | 300.00 | 39 | 0/10 | | DX 8 |
| | | 150.00 | 39 | 0/10 | | |
| | | 600.00 | 34 | 0/10 | | |
| | | 300.00 | 12 | 0/10 | | |
| | | 150.00 | 16 | 0/10 | | |

TABLE 2-continued

| Ex. No. | Dose mg/kg | % Inhib. | Tox/ Tot | Admin (a) | Dose (b) Sched. |
|---|---|---|---|---|---|
| 55 | 150.00 | 75 | 1/10 | | BIDX 8 |
|    | 75.00  | 70 | 0/10 | | |
| 61 | 300.00 | TOX | 10/10 | IP | DX 8 |
|    | 150.00 | 72 | 2/10 | IP | |
|    | 300.00 | 0 | 0/10 | | BIDX 8 |
|    | 150.00 | 0 | 0/10 | | |
| 62 | 50.00  | 99 | 2/10 | | DX 8 |
|    | 25.00  | 98 | 0/10 | | |
| 63 | 50.00  | 95 | 0/10 | | DX 8 |
|    | 25.00  | 79 | 0/10 | | |
| 64 | 300.00 | 43 | 0/10 | IP | DX 8 |
|    | 150.00 | 22 | 0/10 | IP | |
|    | 300.00 | 45 | 0/10 | | BIDX 8 |
|    | 150.00 | 22 | 0/10 | | |
| 65 | 300.00 | 97 | 0/10 | | BIDX 8 |
|    | 150.00 | 91 | 0/10 | | |

(a) Route of Administration unless otherwise indicated compound was administered orally by gavage
IP = intraperitoneal, 0.5 ml (diluted as with oral dose).
IV = intravenous, 0.25 ml (diluted with 10% DMSO, 20% Emulphor EL-620, 70% of 0.9% aqueous NaCl).
(b) Dosage Schedule
DX = daily for indicated number of days
BIDX = twice daily 8 hours apart for the indicated number of days
Days + day number indicates administration of drug occurred on indicated day(s) after implanting of neoplasm
(b-1) Dosage initiated 14 days after implanting neoplasm
(b-2) Dosage initiated 7 days after implanting neoplasm
(b-3) Dosage initiated 5 days after implanting neoplasm
(c) Tumor type HC-1
(d) Tumor type LX1
(e) Tumor type VRC5
(f) Tumor type B-16
(g) Tumor type C3H mammary adenocarcin
(h) Tumor type CA-755 adenocarcinoma
(i) Tumor type colon carcinoma-26
(j) Tumor type CX-1
(k) Tumor type ELC2
(l) Tumor type GC3
(m) Tumor type Lewis Lung Carcinoma
(n) Tumor type M-5 Ovarian Carcinoma
(o) Tumor type MX-1
(p) Tumor type X5563 Plasma Cell Myeloma The compounds of formula 1 are antineoplastic agents and the invention provides a method of treating susceptible neoplasms. In particular the present compounds are useful in treating solid tumors including carcinomas such as ovarian, non-small cell lung, gastric pancreatic, prostate, renal cell, breast, colorectal, small cell lung, melanoma and head and neck; and sarcomas such as Kaposi's sarcoma and rhabdomyosarcoma.

The instant compounds can be administered individually or in combination, preferably orally, and usually in the form of a pharmaceutical composition. The instant compounds can also be used in combination with other chemotherapeutic agents. The pharmaceutical compositions of the instant compounds are prepared in a manner well known in the pharmaceutical art and comprise at least one active compound. Accordingly, the present invention also includes pharmaceutical compositions comprising as active ingredient certain compounds of formula 1 associated with a pharmaceutically acceptable carrier, and the invention further comprises the method of treating susceptible neoplasms using the compositions containing as an active ingredient a compound of formula 1.

In making the compositions of the present invention, as well as compositions containing other compounds of formula 1, the active ingredients are usually mixed with an excipient, diluted by an excipient or enclosed within such a carrier which can be in the form of a capsule, sachet, paper or other container. When the excipient serves as a diluent, it can be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

In preparing a formulation it may be necessary to mill the active compound to provide the appropriate particle size prior to combining with the other ingredients. If the active compound is substantially insoluble, it ordinarily is milled to a particle size of less than about 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agent such as methyland propylhydroxybenzoates, sweetening agents or flavoring agents.

The compositions of the invention can be formulated so as to provide quick, sustained or delayed release of the active ingredient after administration to the patient by employing procedures well known in the art. The compositions are preferably formulated in a unit dosage form, each dosage normally containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are effective over a wide dosage range. For example, dosages per day normally fall within the range of about 0.5 to about 1200 mg/kg of body weight. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, the severity of the patient's symptoms, and therefore the above dosage ranges are not intended to limit the scope of the invention in any way.

The following formulation examples can employ as active compounds any of the compound of formula 1. The examples are illustrative only and are not intended to limit the scope of the invention in any way.

Formulation 1

Hard gelatin capsules are prepared using the following ingredients:

| | Quantity (mg/capsule) |
|---|---|
| Example 2 | 250 |
| Starch | 305 |
| Magnesium stearate | 5 |

The above ingredients are mixed with and filled into hard gelatin capsules in 560 mg quantities.

Formulation 2

A tablet formula is prepared using the ingredients below:

|  | Quantity (mg/tablet) |
|---|---|
| Example 3 | 250 |
| Cellulose, microcrystalline | 400 |
| Colloidal Silicon dioxide | 10 |
| Stearic acid | 5 |

The components are blended and compressed to form tablets each weighing 665 mg.

Formulation 3

A dry powder inhaler formulation is prepared containing the following components:

|  | Weight % |
|---|---|
| Example 4 | 5 |
| Lactose | 95 |

The active compound is mixed with the lactose and the mixture added to a dry powder inhaling applicance.

Formulation 4

Tablets each containing 60 mg of active ingredient are made up as follows:

| Example 6 | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mq |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50°-60° C. and passed through a No. 16 mesh U.S. sieve. The sodium carboxymethyl starch, magnesium stearate and talc, previously passed through a No. 30 mesh sieve, are then added to the granules which, after mixing, are compressed on a tablet machine to yield tablet each weighing 150 mg.

Formulation 5

Capsules each containing 80 mg of medicament are made as follows:

| Example 17 | 80 mg |
|---|---|
| Starch | 109 mg |
| Magnesium stearate | 1 mg |
| Total | 190 mg |

The active ingredient, cellulose, starch and magnesium stearate are blended, passed through a No. 20 mesh U.S. sieve, and filled into hard gelatin capsules in 190 mg quantities.

Formulation 6

Suppositories each containing 225 mg of active ingredient are made as follows:

| Example 16 | 225 mg |
|---|---|
| Saturated fatty acid glycerides to | 2,000 mg |

The active ingredient is passed through a No. 60 mesh U.S. sieve and suspended in the saturated fatty acid.

Formulation 7

Suspensions each containing 50 mg of medicament per 5 ml dose are made as follows:

| Example 20 | 50 mg |
|---|---|
| Xanthan Gum | 4 mg |
| Sodium carboxymethyl cellulose (11%) Microcrystalline Cellulose (89%) | 50 mg |
| Sucrose | 1.75 g |
| Sodium Benzoate |  |
| Flavor | q.v. |
| Color | q.v. |
| Purified water to | 5 ml |

The medicament, sucrose and xanthan gum are blended, passed through a No. 10 mesh U.S. sieve, and then mixed with a previously made solution of the microcrystalline cellulose and sodium carboxymethylcellulose in water. The sodium benzoate, flavor and) color are diluted with some of the water and added with stirring. Sufficient water is then added to produce the required volume.

Formulation 8

Capsules each containing 150 mg of medicament are made as follows:

| Example 33 | 150 mg |
|---|---|
| Starch | 407 mg |
| Magnesium stearate | 3 mq |
| Total | 560 mg |

The active ingredient, cellulose, starch and magnesium stearate are blended, passed through a No. 20 mesh U.S. sieve, and filled into hard gelatin capsules in 560 mg quantities.

We claim:

1. A compound of the formula

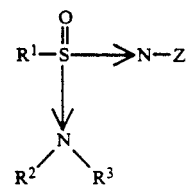

wherein $R^1$ is

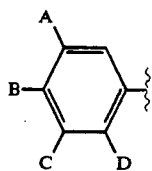

wherein A, B and C are independently; (a) H with the proviso that at least one of A, B or C is other than H; (b) chlorine, bromine or iodine; (c) $CH_3$ or $CH_2CH_3$; (d) —C(O)$R^a$, wherein $R^a$ is H or $C_1$–$C_5$ alkyl; (e) —$(CH_2)_nOR^b$ wherein n is 1–4 and $R^b$ is H or C(O)$R^c$ wherein $R^c$ is $C_1$–$C_4$ alkyl; or (f) A and B or B and C together are (i) —$(CH_2)_q$— wherein q is 3 or 4, (ii) $(CH_2)_mO(CH_2)_b$ wherein m is 0 or 1 and b is 1, 2 or 3 with the proviso that b is 2 or 3 when m is O, or (iii) —O—$(CH_2)_n$—O— wherein n is 1 or 2, and C or A respectively is H or $CH_3$; and D is H, chlorine, bromine, iodine, $CH_3$ or $CH_2CH_3$, and $R^2$ is H, $C_1$–$C_8$ alkyl with the proviso that except for the isopropyl group there is no branching in the alpha-position, $C_3$–$C_8$ alkenyl, $(CH_2)_nOH$ wherein n is 1–5, —$(CH_2)_pC_6H_5$ wherein p is 1–3, or —C(O)$R^d$ wherein $R^d$ is H or $C_1$–$C_4$ alkyl;

$R^3$ is H or $CH_3$;

Z is

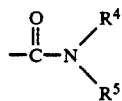

wherein $R^4$ is hydrogen, methyl, or —C(O)$R^a$ wherein $R^a$ is hydrogen or $C_1$–$C_5$ alkyl;

$R^5$ is

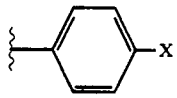

wherein X is chlorine, bromine, iodine or $CH_3$; or a tautomer or pharmaceutically acceptable salt thereof.

2. The compound of claim 1 wherein Z is C(O)$NR^4R^5$.

3. The compound of claim 2 wherein A, B and C are independently: (a) H with the proviso that at least one of A, B or C is not H; (b) methyl or ethyl; (c) C(O)$R^a$ wherein $R^a$ is H or $C_1$–$C_3$ alkyl; (d) $(CH_2)_nOR^b$ wherein n is 1–2 and $R^b$ is H or C(O)$R^c$ wherein $R^c$ is $C_1$–$C_2$ alkyl; or C is H or $CH_3$ and A and B together are $(CH_2)_q$ wherein q is 3 or 4, with the additional proviso that at least one of A, B or C is H, or methyl;

D is H;

$R^2$ is H, $C_1$–$C_6$ alkyl with the proviso that except for the isopropyl group there is no branching at the alpha position, $C_3$–$C_6$ alkenyl, or C(O)$R^d$ is $C_1$–$C_3$ alkyl; and $R^5$ is chlorine, bromine or methyl; and pharmaceutically acceptable salts thereof.

4. The compound of claim 3 wherein A, C and D are H and B is selected from the group consisting of chlorine, bromine, methyl, ethyl, C(O)$R^a$ wherein $R^a$ is hydrogen or $C_1$–$C_3$ alkyl, and $(CH_2)_nOR^b$ wherein n is 1 or 2 and $R^b$ is C(O)$R^c$ wherein $R^c$ is $C_1$–$C_2$ alkyl.

5. The compound of claim 2 wherein $R^2$ is H, $C_1$–$C_6$ alkyl with the proviso that except for isopropyl there is no branching in the alpha position, $C_3$–$C_6$ alkenyl, or C(O)$R^d$ wherein $R^d$ is $C_1$–$C_2$ alkyl.

6. The compound of claim 2 wherein A, B and C are independently: (a) H with the proviso that at least one of A, B or C is other than H; (b) chlorine or bromine; (c) methyl or ethyl; (d) C(O)$R^a$ wherein $R^a$ is H or $C_1$–$C_4$ alkyl; (e) $(CH_2)_nOR^b$ wherein n is 1–2 and $R^b$ is H or C(O)$R^c$ wherein $R^c$ is $C_1$–$C_2$ alkyl; or (f) A and B together are $(CH_2)_q$ wherein q is 3 or 4 with the proviso that C and D are not C(O)$R^a$ or $(CH_2)_nOR^b$ and with the further proviso no more than one of A, B and C is substituted with C(O)$R^a$ or $(CH_2)_nOR^b$.

7. The compound of claim 1 which is (p-$CH_3C_6H_4$)S(O)($NH_2$)NC(O)(NH)(p-$ClC_6H_4$).

8. A compound selected from the group consisting of N-[[(4-chlorophenyl)amino]carbonyl]-4-methylbenzenesulfonimidamide; N-[[(4-chlorophenyl)amino]carbonyl]-N'-4-dimethylbenzenesulfonimidamide; N-[[(4-chlorophenyl)amino]carbonyl]-N'-ethyl-4-methylbenzenesulfonimidamide; N-[[(4-chlorophenyl)amino]carbonyl]-N'-(1-methylethyl)-4-methylbenzenesulfonimidamide; N-[[(4-chlorophenyl)amino]carbonyl]-N'-butyl-4-methylbenzene-sulfonimidamide; N-[[(4-chlorophenyl)amino]carbonyl]-N'-acetyl-N-methyl-4-methylbenzenesulfonimidamide; N-methyl-N-[[(4-chlorophenyl)amino]carbonyl]-4-methyl-benzenesulfonimidamide; N-[[(4-chlorophenyl)amino]carbonyl]-4-methylbenzenesulfonimidamide; N-[[(4-chlorophenyl)amino]carbonyl]-4-ethylbenzene-sulfonimidamide; N-[[(4-chlorophenyl)amino]carbonyl]-N'-(2-methyl)-propyl(4-methyl)benzenesulfonimidamide; N-[[(4-chlorophenyl)amino]carbonyl]-4-chlorobenzene-sulfonimidamide; N-[[(4-chlorophenyl)amino]carbonyl]-3,4-dimethylbenzenesulfonimidamide; N-[[(4-chlorophenyl)amino]carbonyl]-3,4,5-trimethylbenzenesulfonimidamide; N-[[(4-chlorophenyl)amino]carbonyl]-4-(acetoxymethyl)benzenesulfonimidamide; N-[[(4-chlorophenyl)amino]carbonyl]-4-(hydroxymethyl)benzenesulfonimidamide; N-[[(4-chlorophenyl)amino]carbonyl]-4-formylbenzenesulfonimidamide; N-[[(4-chlorophenyl)amino]carbonyl]-5-indanylsulfonimidamide; N-[[(4-chlorophenyl)amino]carbonyl]-N'-methyl-5-indanylsulfonimidamide; and N-[[(4-chlorophenyl)amino]carbonyl]-N'-methyl-3,4-dimethylbenzenesulfonimidamide; and tautomers and pharmaceutically acceptable salts thereof.

9. A compound of the formula

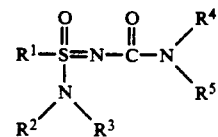

wherein $R^1$ is

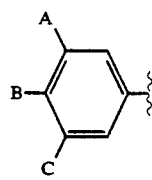

wherein A, B, and C are independently;
 a) H with the proviso that at least one of A, B or C is other than H;
 b) chlorine or bromine;
 c) $CH_3$ or $CH_2CH_3$;
 d) $C(O)R^a$, wherein $R^a$ is H or $C_1$-$C_5$ alkyl;
 e) $(CH_2)_nOR^b$ wherein n is 1-4 and $R^b$ is H or $C(O)R^c$ wherein $R^c$ is $C_1$-$C_4$ alkyl; or
 f) C is H or $CH_3$ and A and B together are
  1) —$(CH_2)_q$— wherein q is 3 or 4,
  2) $(CH_2)_mO(CH_2)_b$ wherein m is 0 or 1 and b is 1, 2 or 3 with proviso that b is 2 or 3 when m is O, or
  3) —O—$(CH_2)_n$—O— wherein n is 1 or 2; with the further proviso that no more than two of A, B or C is $C(O)R^a$, $(CH_2)_nOR^b$ or $C(O)R^c$;

$R^2$ is H, $C_1$-$C_6$ alkyl with the proviso that except for the isopropyl group there is no branching in the alpha-position, $C_3$-$C_6$ alkenyl, $(CH_2)_nOH$ wherein n is 1-5, $(CH_2)_pC_6H_5$ wherein p is 1-3, or $C(O)R^d$ wherein $R^d$ is H or $C_1$-$C_4$ alkyl;

$R^3$ is H or $CH_3$;

$R^4$ is H or $Ch_3$;

$R^5$ is

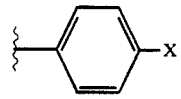

wherein X is chlorine, bromine, iodine or $CH_3$; or a tautomer or a pharmaceutically acceptable salt thereof.

10. The compound of claim 9 wherein A, B and C are independently
 a) H with the proviso that at least one of A, B or C is other than H;
 b) chlorine;
 c) $CH_3$ or $CH_2CH_3$; or
 d) $(CH_2)_nOR^b$ wherein n is 1 or 2 and $R^b$ is $C(O)R^c$ wherein $R^c$ is $C_1$-$C_3$ alkyl;

$R^2$ is H, $C_1$-$C_6$ alkyl with the proviso that except for the isopropyl group there is no branching in the alpha-position, or $C(O)R^d$ wherein $R^d$ is $C_1$-$C_3$ alkyl; and X is chlorine or bromine.

11. A method for treating susceptible neoplasms in mammals which comprises administering to a mammal in need of such treatment an effective amount of a compound of claim 1.

12. The method of claim 11 wherein said neoplasms is ovarian, non-small cell lung, gastric, pancreatic, prostatic, renal cell, breast, colorectal, small-cell lung, melanoma, head and neck, kaposis sarcoma, or rhabdomyosarcoma.

13. The method of claim 11 wherein said neoplasm is ovarian, non-small cell lung, renal, melanoma or breast.

14. A pharmaceutical formulation comprising a compound of claim 1 or a pharmaceutically acceptable salt thereof in combination with a pharmaceutically acceptable excipient therefor.

15. A pharmaceutical formulation comprising a compound of claim 9 or a pharmaceutically acceptable salt thereof in combination with a pharmaceutically acceptable excipient therefor.

* * * * *